(12) United States Patent
Takeuchi

(10) Patent No.: US 10,799,396 B2
(45) Date of Patent: Oct. 13, 2020

(54) DISPOSABLE DIAPER

(71) Applicant: Daio Paper Corporation, Ehime (JP)

(72) Inventor: Tomonari Takeuchi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 610 days.

(21) Appl. No.: 15/547,428

(22) PCT Filed: Jan. 29, 2016

(86) PCT No.: PCT/JP2016/052810
§ 371 (c)(1),
(2) Date: Dec. 4, 2017

(87) PCT Pub. No.: WO2016/121980
PCT Pub. Date: Aug. 4, 2016

(65) Prior Publication Data
US 2018/0147094 A1 May 31, 2018

(30) Foreign Application Priority Data

Jan. 30, 2015 (JP) .................................. 2015-017498
Sep. 30, 2015 (JP) ................................. 2015-195460

(51) Int. Cl.
*A61F 13/49* (2006.01)
*A61F 13/496* (2006.01)
(Continued)

(52) U.S. Cl.
CPC ........ *A61F 13/15203* (2013.01); *A61F 13/15* (2013.01); *A61F 13/15739* (2013.01);
(Continued)

(58) Field of Classification Search
CPC .......... A61F 13/15203; A61F 13/49011; A61F 13/49012; A61F 13/49017; A61F 13/4906;
(Continued)

(56) References Cited

U.S. PATENT DOCUMENTS 6,572,595 B1    6/2003  Klemp
6,676,647 B2 *  1/2004  Shimada ............... A61F 13/496
                                                    604/385.11
(Continued)

FOREIGN PATENT DOCUMENTS

EP          3202383 A1    8/2017
JP       10-029259 A      2/1998
(Continued)

*Primary Examiner* — Catharine L Anderson
(74) *Attorney, Agent, or Firm* — Muncy, Geissler, Olds & Lowe, P.C.

(57) ABSTRACT

An absorbent article includes a stretchable sheet that is a laminate of a non-stretchable first sheet layer, a non-stretchable second sheet layer, and an elastic film disposed between the first and second sheet layers, and the elastic film is stretchable at least in the front-back direction. The first sheet layer is bonded to the second sheet layer at a large number of joints directly or through the elastic film and the joints are arrayed at intervals. The stretchable sheet is contracted by a contraction force of the elastic film and can be stretched by an external force applied in the front-back direction. The leg portion is also contracted by a contraction force of the elastic film and can be stretched by an external force applied in the width direction. The leg portions and adjoined regions have different joint area rates and thereby have different stretching stresses.

4 Claims, 22 Drawing Sheets

(51) Int. Cl.
*A61F 13/15* (2006.01)
*A61F 13/513* (2006.01)
*A61F 13/51* (2006.01)

(52) U.S. Cl.
CPC ...... *A61F 13/496* (2013.01); *A61F 13/49017* (2013.01); *A61F 13/513* (2013.01); *A61F 2013/15325* (2013.01); *A61F 2013/15406* (2013.01); *A61F 2013/15869* (2013.01); *A61F 2013/49093* (2013.01); *A61F 2013/51078* (2013.01); *A61F 2013/51338* (2013.01)

(58) Field of Classification Search
CPC .............. A61F 13/49061; A61F 13/515; A61F 2013/15325; A61F 2013/49022; A61F 2013/49033; A61F 2013/51078; A61F 2013/5108; A61F 2013/51083; A61F 2013/51085; A61F 2013/53991
See application file for complete search history.

(56) References Cited

U.S. PATENT DOCUMENTS

| | | |
|---|---|---|
| 2002/0016122 A1 | 2/2002 | Curro |
| 2010/0168705 A1 | 7/2010 | Stabelfeldt et al. |
| 2010/0215923 A1 | 8/2010 | Frost |
| 2011/0319853 A1 | 12/2011 | Yamashita |

FOREIGN PATENT DOCUMENTS

| | | |
|---|---|---|
| JP | 2003-025471 | 1/2003 |
| JP | 2003025471 A | 1/2003 |
| JP | 2004532758 A | 10/2004 |
| JP | 2005007188 A | 1/2005 |
| JP | 3667353 B2 | 7/2005 |
| JP | 3667353 B2 | 7/2005 |
| JP | 2008260131 A | 10/2008 |
| JP | 4508885 B2 | 7/2010 |
| JP | 4562391 B2 | 8/2010 |
| JP | 2010195044 A | 9/2010 |
| JP | 2010200974 A | 9/2010 |
| JP | 2010-233885 | 10/2010 |
| JP | 2010233885 A | 10/2010 |
| JP | 4934835 B2 | 5/2012 |
| JP | 4954412 B2 | 6/2012 |
| JP | 4954412 B2 | 6/2012 |
| JP | 2014-520589 | 8/2014 |
| JP | 2014150917 A | 8/2014 |
| JP | 2014520589 A | 8/2014 |
| JP | 2016140477 | 8/2016 |
| JP | 2016-185265 A | 10/2016 |
| JP | 6383712 B2 | 8/2018 |
| WO | WO0145616 | 6/2001 |
| WO | WO2008-066006 | 6/2008 |
| WO | WO200806606 A1 | 6/2008 |
| WO | WO2008/126708 A1 | 10/2008 |
| WO | WO2011/048512 | 4/2011 |
| WO | WO2013002691 A1 | 1/2013 |

* cited by examiner

MD

MD (a)

(b)

(c)

(a)

(b)

DISPOSABLE DIAPER

TECHNICAL FIELD

The present invention relates to a disposable diaper that includes a stretchable sheet including a first sheet layer, a second sheet layer, and an elastic film disposed therebetween.

BACKGROUND ART

In absorbent articles, for example, disposable diapers, elastic characteristics are typically imparted to leg portions, waist portions, and the like to improve fitness to the surfaces of bodies. A typical approach to impart elastic characteristics is fixing of elongated elastically stretchable members, such as rubber threads, in a state stretched in the longitudinal direction. In order to impart elasticity over a certain range of width, rubber threads are disposed and fixed in the width direction at intervals in some embodiments.

Articles including a plurality of rubber threads disposed in parallel have different tightening forces between the rubber threads and their surroundings, urge the skin of a wearer in a stripe pattern, and thus impair the texture. Such a disadvantage is noticeable in sensitive waist of the wearer.

In order to impart elastic characteristics to a planar sheet in view of texture, laminates of nonwoven fabric/elastomer film/nonwoven fabric have also been proposed (for example, refer to Patent Literature 1).

Since the stretchable sheet disclosed in Patent Literature 1 is produced by a continuous process, a thermally welding roll for forming bonding portions has a protrusion pattern that is uniform in the width direction and the circumferential direction, and the resulting stretchable sheet has a uniform stretching stress at different positions.

Even if the intermediate regions in the front-back direction of this stretchable sheet are cut away at both sides, the leg portions have the same stretching stress as that of the other regions and thus do not have fitness being satisfactory for the leg portions.

CITATION LIST

Patent Document

Patent Document 1: Japanese Patent No. 4562391

SUMMARY OF INVENTION

Technical Problem

An object of the present invention is to provide a disposable diaper having leg portions with satisfactory fitness.

Solution to Problem

The present invention that solves the disadvantage described above has the following configuration.
<Basic Configuration>
The disposable diaper of the present invention has a stretchable region ventrodorsally, which is stretchable in the width direction.

The disposable diaper has an intermediate region between front and rear torso regions and leg portions narrowed toward the center side in the width direction from the inner end points of the torso region in the front-back direction over the intermediate region.

A back sheet for the above ventrodorsal region is a stretchable sheet. The stretchable sheet is a laminate of a non-stretchable first sheet layer, a non-stretchable second sheet layer, and an elastic film stretchable in the width direction disposed therebetween. The first sheet layer is bonded to the second sheet layer at a large number of joints directly or through the elastic film and the joints are arrayed at intervals.

The stretchable sheet is contracted by a contraction force of the elastic film and can be stretched by an external force applied in the width direction.

The leg portion is also contracted by a contraction force of the elastic film and can be stretched by an external force applied in the width direction.

In the present invention, the leg portions and regions adjoined to the leg portions preferably have different joint area rates that indicate the rates of the total areas of the joints contained in the unit area.

A small joint area rate leads to a large stretching stress. A combination of leg portions with small joint area rates causing large stretching stresses and regions adjoined to the leg portions with large joint area rates causing small stretching stresses generates large stretching force acting on the leg portions, and thus produces a diaper having satisfactory fitness.

Alternatively, the joint area may vary within the leg portion.

For example, the joint area rate that indicates the rate of the total area of joints contained in the unit area may differ between a section of the leg portion closer to the inner end point of the torso region in the front-back direction and a section of the leg portion closer to the center side of the intermediate region.

The joint area rate in the specification can be determined by the dimension, shape, interval, and geometry in the length and circumferential geometries of the anvil roll.

In this case, the section of the leg portion closer to the inner end point (the section Z1 in FIG. 15(*b*)) in the front-back direction of the torso region has a joint geometry that facilitates stretching in the width direction and the section of the leg portion closer to the center side of the intermediate region (the section Z2 in FIG. 15(*b*)) has a joint geometry that facilitates stretching in the diagonally upward direction.

A section adjacent to the leg line of the leg portion has a small joint area rate causing a large stretching stress, whereas a section remote from the leg line of the leg portion has a large joint area rate causing a small stretching stress.

This configuration results in a larger stretching force acting on the section adjacent to the leg line of the leg portion and thus satisfactory fitness.

The joints in the present invention may have any geometry. A preferred example is a staggered arrangement.

In the stretchable sheet in the present invention, the first sheet layer and the second sheet layer have no through hole. This configuration differs from the stretchable sheet shown in FIG. 5 or 7 in Japanese Patent No. 4562391.

The joints in the stretchable region of the present invention are formed by the following scheme:

(1) The first sheet layer and the second sheet layer partially melts and then adhere to the elastic film. In this scheme, the first sheet layer and the second sheet layer are bonded through the elastic film;

(2) The elastic film melts and then migrates into the first sheet layer and the second sheet layer. In this scheme, the first sheet layer directly adheres to the second sheet layer without intervention of the elastic film; and (3) This scheme is an intermediate between schemes (1) and (2). Although the two surfaces of the elastic film partially melt and then migrate into the first sheet layer and the second sheet layer, the rest of the elastic film still remains. In this scheme, the first sheet layer adheres to the second sheet layer through the remaining elastic film.

Schemes (2) and (3) among these schemes cause a difference in strength between the joints and the non-joint regions. If the product is stretched mechanically or manually after the stretched state of the stretchable sheet is released to be contracted or after the stretched sheet is bonded to any other member and then the stretched state is released to be contracted, the stretchable sheet ruptures at boundaries between the joints and non-joint regions. As a result, through holes are formed.

In such a case, the elastic film stretchable at least in the width direction is disposed between the non-stretchable first sheet layer and the non-stretchable second sheet layer in the stretchable region, and the first sheet layer are bonded to the second sheet layer at a large number of joints disposed at intervals via the through holes formed in the elastic film.

The through holes have an advantage of air permeability. All joints need not have through holes, and through holes formed in parts of the joints have air permeability. In the case that the elastic film is stretchable only in the width direction, the through holes extend from the fringes of the joints in the width direction. In the case that the elastic film is stretchable in the width direction and the perpendicular direction, through holes extend from the fringes of the joints or circular through holes extend around the joints, in some cases.

In some embodiments, the joints have a length in the perpendicular direction larger than the length in the width direction.

In the case that the melting point of the elastic film is lower than the melting point of the first sheet layer composed of nonwoven fabric and the melting point of the second sheet layer composed of nonwoven fabric, a melting energy corresponding to a temperature higher than the melting point of the elastic film and lower than the melting points of the first and second sheet layers causes thermal melting of the elastic film and no or partial melting of the first and second sheet layers. Thus, the holes are not formed in the entire joint regions, and the first sheet layer and the second sheet layer remain.

The stretchable sheet is produced at a high line rate. Even if the melting energy corresponding to the temperature higher than the melting points of the first and second sheet layers is applied, the first and second sheet layers do not melt or partially melt and thus the through holes are not formed in the entire joint regions.

In such a view, it is preferred that the elastic film have a melting point of approximately 80° C. to approximately 145° C., the first sheet layer and the second sheet layer have melting points of approximately 85° C. to approximately 190° C., in particular approximately 130° C. to approximately 190° C., and the difference between the melting points of the first and second sheet layers and the melting point of the elastic film 30, which is lower than those of the first and second sheet layers, be approximately 50° C. to approximately 80° C.

In a preferred embodiment, the elastic film has a melting point of 95° C. to 125° C., the first sheet layer has a melting point of more than 125° C. to 160° C., more preferably 130° C. to 160° C., and the second sheet layer has a melting point of more than 125° C. to 160° C., more preferably 130° C. to 160° C.

Preferred joints each have an area of 0.14 to 3.5 mm$^2$ in the stretchable region, the through holes in the natural-length state have an opening area that is 1 to 1.5 times the area of the joints, and the area rate of the joints in the stretchable region is 1.8 to 22.5%.

The term "area rate" indicates the rate of the target portion per the unit area, i.e., the total area of the target portions (for example, joints and openings of the through holes) divided by the area of the target region (for example, stretchable region) in percentage. In particular, the term "joint area rate" indicates the area rate when the structure is stretched to elastic limit in the stretchable direction. The opening area of the through holes indicates the value when the stretchable structure is a natural-length state and indicates a minimum value in the case the opening area of the through holes is uneven in the thickness direction, for example, between the front and back faces of the elastic film.

The term "stretching stress" indicates "the stress (N/35 mm) when the sample is stretched to 50% of the elastic limit" that is measured by a tensile test at an initial chuck interval (distance between marked lines) of 50 mm and a speed of testing of 300 mm/min in accordance with JIS K7127:1999 "Plastic—Determination of tensile properties". If a sample with a width of 35 mm cannot be prepared, the test piece with a maximum possible width is prepared and the observed value is converted into a value at a width of 35 mm.

Even if a sufficiently large test piece cannot be prepared from a target region with a small area, small test pieces can also be used for comparison of the stretching stress.

Since the stretching stress varies at different sites in the region, appropriate sampling of the test pieces is important. In place of determination of the absolute value of the stretching stress, test pieces with any size are prepared from different sites and stretching stresses at 100% to 150% elongation of the natural state of these pieces are compared for relative evaluation.

Advantageous Effects

As described above, the disposable diaper of the present invention has leg portions with satisfactory fitness.

DESCRIPTION OF EMBODIMENTS

The embodiments of the present invention will now be described in detail with reference to the accompanying drawings.

Figure 7:
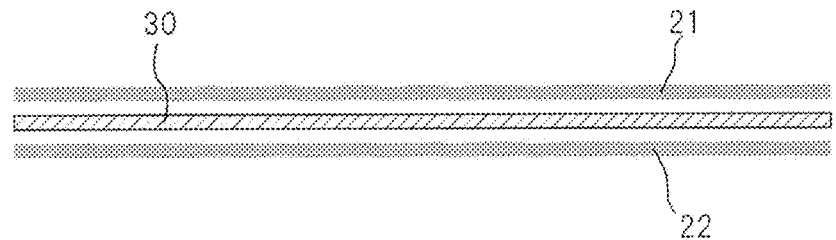
FIG. 7 is a cross-sectional view illustrating a stretchable sheet before bonding.
Figure 8:
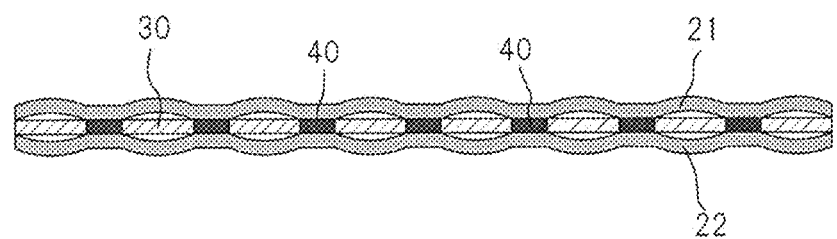
FIG. 8 is across-sectional view illustrating a stretchable sheet after bonding.
Figure 9:
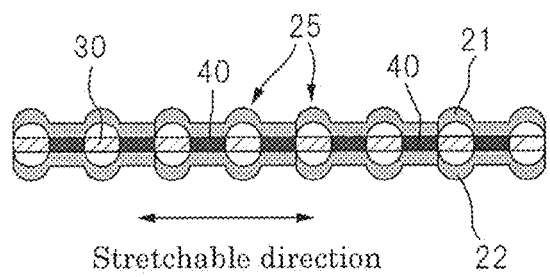
FIG. 9 is a cross-sectional view illustrating a stretchable sheet after contracted.

The disposable diaper of the present invention has a stretchable region in the width direction. With reference to FIGS. 7 to 9, the stretchable region is composed of a laminate of a first sheet layer 21 of, for example, non-stretchable nonwoven fabric and a second sheet layer 22 of, for example, non-stretchable nonwoven fabric and an elastic film 30 disposed between the first sheet layer 21 and the second sheet layer 22 and being stretchable in the width direction. The first sheet layer 21 and the second sheet layer 22 are bonded to each other directly or through the elastic film 30 at a large number of joints 40 arrayed at intervals.

The term "non-stretchable" regarding the first sheet layer 21 and the second sheet layer 22 does not indicate that these layers are completely non-stretchable but substantially non-stretchable in comparison with the stretchable characteristics of the elastic film.

Figure 10:
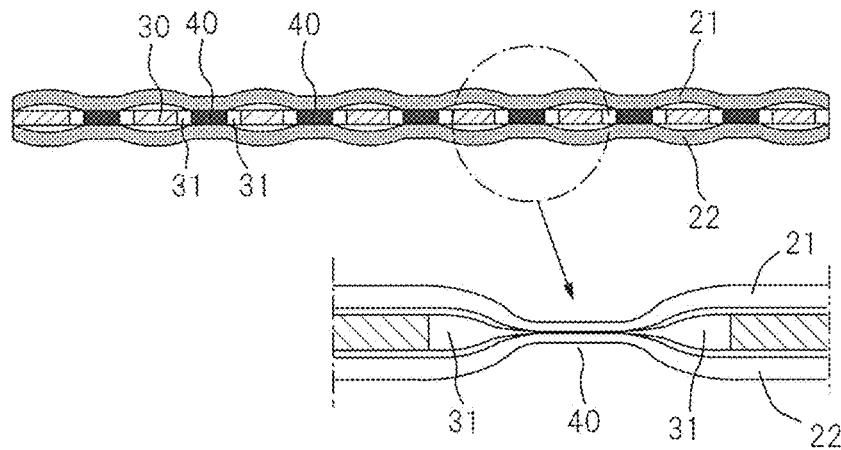
FIG. 10 is a cross-sectional view illustrating a stretchable sheet having through holes after bonding.
Figure 11:
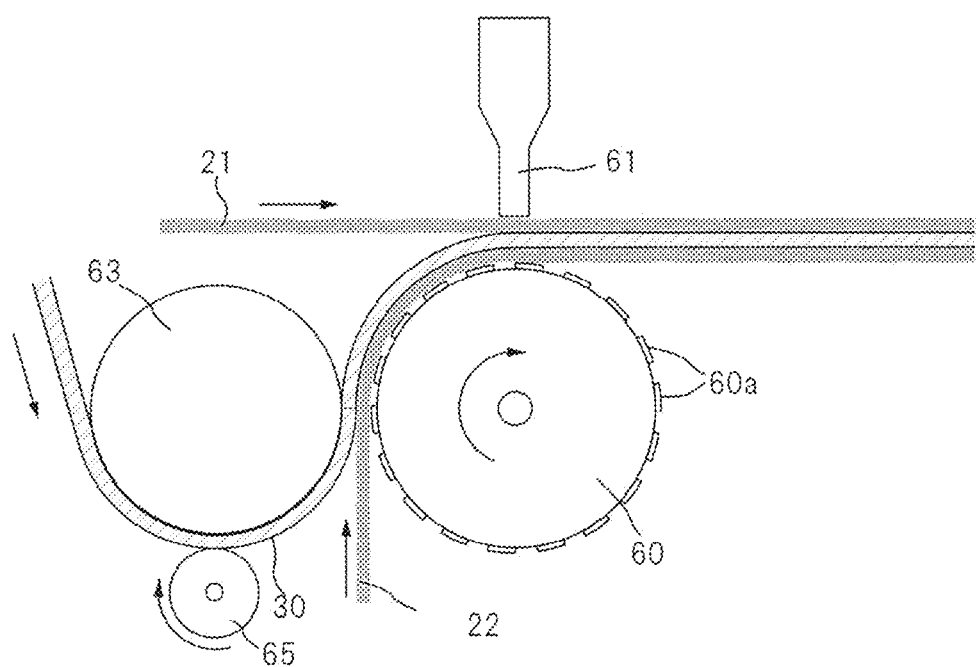
FIG. 11 is an outline view of stretching and bonding means.

With reference to FIG. 10, the first sheet layer 21, the elastic film 30, and the second sheet layer 22 are fed between an anvil roll 60 having a predetermined pattern of protrusions 60a on its surface and an ultrasonic horn 61, and the elastic film 30 is primarily melt by ultrasonic melting energy from the ultrasonic horn 61 to bond the first sheet layer 21 and the second sheet layer 22.

The anvil roll 60 faces a counter roll 63. The counter roll 63 is driven by a driving roll 65 that works as a nip roll to pinch the elastic film 30.

In such a structure, the elastic film 30 travels around the counter roll 63, passes through the nip to the driving roll 65, and then travels around the anvil roll 60.

The circumferential velocity of the driven anvil roll 60 is controlled to be larger than the circumferential velocity of the driving roll 65 (or the circumferential velocity of the counter roll 63) to stretch the elastic film 30 and to bond the two sheet layers by the effect of the protrusions 60a of the anvil roll 60 and the ultrasonic horn 61.

The difference in circumferential velocity between the anvil roll 60 and the driving roll 65 can be appropriately determined to control the stretch rate (on the basis of the length, 100%, in the natural state) of the elastic film 30 in the manufacturing process.

FIG. 8 is a schematic cross-section of the stretchable sheet after bonding in a stretched state. When the stretchable sheet is released from the stretched state, the sheet contracts by the contraction force of the elastic film 30 as shown in a schematic view of FIG. 9. An external force in the width direction (horizontal direction in FIG. 9) enables the sheet to stretch. In the case that the stretchable sheet is used ventro-dorsally in the disposable diaper, the sheet contracts a waist portion or a portion thereunder.

Since this stretchable sheet can be produced so as to have a predetermined area, the sheet can be used so that the contraction force is applied to the entirety of a desired area. In this regard, a traditional disposable diaper is usually composed of a plurality of rubber threads fixed in parallel. Such a configuration leads to low-quality products due to deterioration of hot melt adhesive for bonding the rubber threads and the sheet and instable production. The stretchable sheet of the present invention can solve such disadvantages of the traditional products.

As can be seen in a contracted state of FIG. 9, the stretchable sheet has outer faces provided with regular fine wrinkles or wimples; hence, a wearer feels soft touch to the skin.

In the embodiment described above, the first sheet layer 21 and the second sheet layer 22 are bonded by melting of the elastic film 30. In this case, (1) the first sheet layer 21 or second sheet layer 22 is bonded at the surface of the elastic film 30; (2) the surface of the elastic film 30 is melted and then transfused into interstices between fibers of the first sheet layer 21 and second sheet layer 22; or (3) the substantially entire elastic film 30 is melted and then transfused into interstices between fibers of the first sheet layer 21 and the second sheet layer 22. The present invention, however, may have any other interlayer bonding process.

In Embodiment (3) of these embodiments, the first sheet layer 21 and the second sheet layer 22 are directly bonded without intervention of the elastic film.

In Embodiments (1) to (3), the melting point of the elastic film 30 is lower than that of the first sheet layer 21 and that of the second sheet layer 22. Alternatively, the melting point of the elastic film 30 may be higher than that of the first sheet layer 21 and that of the second sheet layer 22. In this case, the surface in contact with the elastic film 30 of the first sheet layer 21 and/or the second sheet layer 22 is activated or melted and then bonded to the elastic film 30.

In an embodiment, the first sheet layer 21 and/or the second sheet layer 22 may also be melted in addition to partial melting of the elastic film 30 for bonding.

The first sheet layer 21 and/or second sheet layer 22 may be composed of nonwoven fabric and fibers of the fabric have a core-shell structure. In this case, for example, the shell component of the fiber may be melted for bonding.

In domains of the stretchable sheet, the joint area rate indicating the rate of total area of the joints contained in the unit area preferably varies in the front-back direction of the disposable diaper for different stretching stresses.

Figure 1:
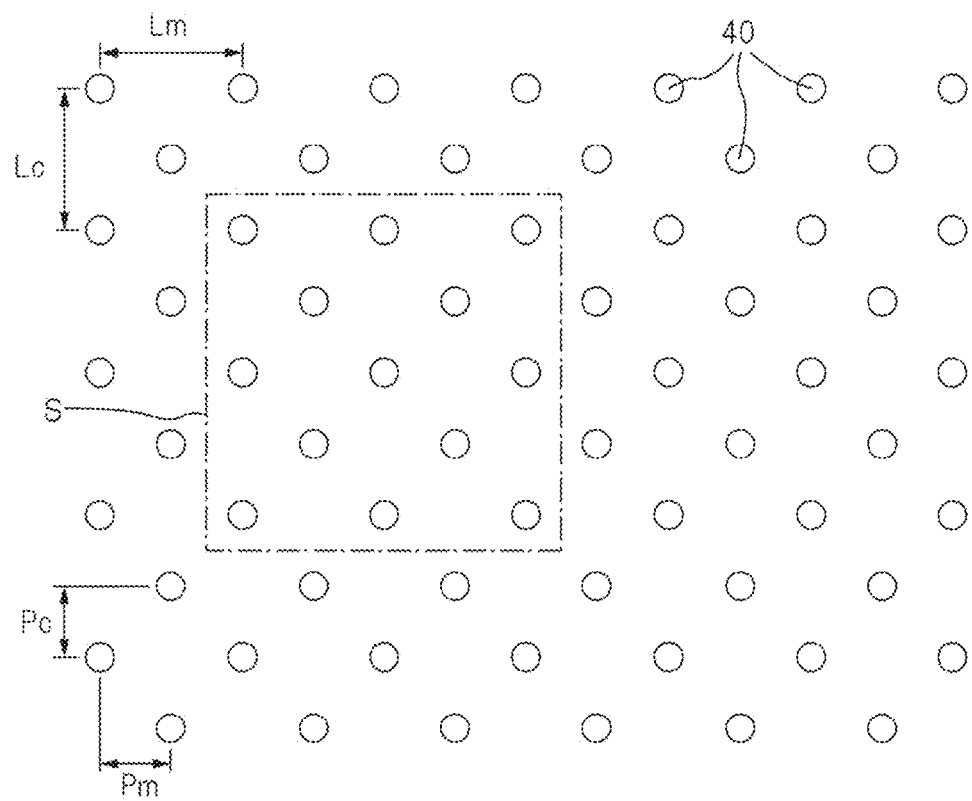
FIG. 1 is a plan view of example geometry of joints.

With reference to FIG. 1, the joint area rate is expressed in percentage of the total area of the joints 40, 40 . . . contained in the unit area S to the unit area S. In such a case, the unit area S should preferably be determined so as to contain 10 or more joints (a smaller number precludes comparison of stretching stress). The embodiment shown in FIG. 1 contains 13 joints. The shape defining the unit area S may be square or any other shape, for example, rectangle or circle.

The joint 40 has a circular shape, as shown in FIG. 1, in an embodiment. Other shapes such as ellipsoidal and rectangular shapes are also available. In FIG. 1, Lm indicates the array interval in the machine direction; Lc indicates the array interval in the cross direction perpendicular to the machine direction; Pm indicates the pitch length in the machine direction (MD); and Pc indicates the pitch length in the cross direction (CD).

FIGS. 2 to 6 illustrate domains having different joint area rates in the stretchable sheet.

Figure 2:
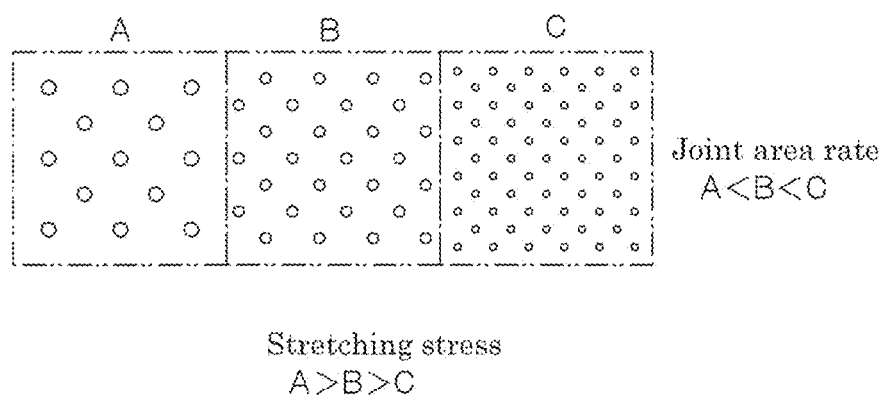
FIG. 2 is an outline plan view of an example configuration of domains for joints having different area rates.

In FIG. 2, the joint area rate is set to domain A<domain B<domain C, so that the stretching stress holds the relation: domain A>domain B>domain C.

For example, domain A with a long pitch lengths Pm and Pc is compared with domain C with a short pitch lengths Pm and Pc. Domain A with a long pitch lengths Pm and Pc (low joint area rate) has a larger stretch rate than domain C with a short pitch lengths Pm and Pc. As a result, the stretching stress holds the relation: domain A>domain B>domain C. Domain B represents an intermediate domain.

In the embodiment shown in FIG. 2, the domains have different stretching stresses; hence, these domains have different contraction forces. This is useful when the absorbent article is worn.

Figure 3:
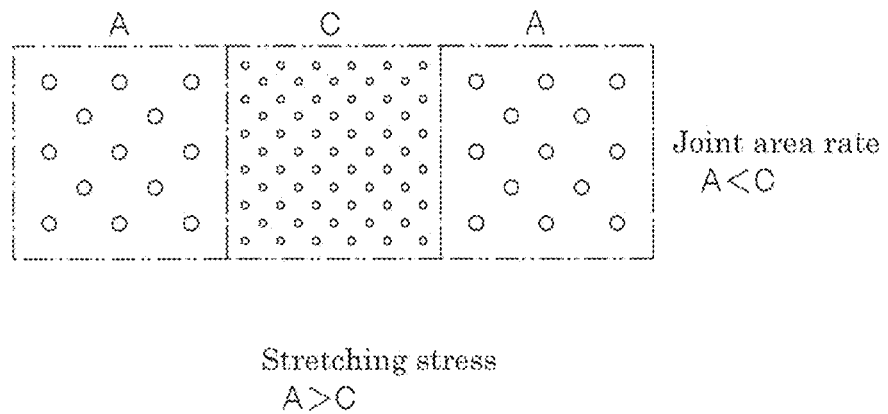
FIG. 3 is an outline plan view of another example configuration of domains for joints having different area rates.

In the case of FIG. 3, the stretching stress of the intermediate domain is smaller than that of the two side domains in the transverse direction in the drawing. This configuration enables effectively these domains to be used for a disposable diaper ventrodorsally in which the intermediate domain lies in a region for an absorber in the diaper, to reduce the stretching stress or to have substantially no elastic characteristics while the side domains (for side portions of the disposable diaper) have sufficient stretching stress. This disposable diaper can comfortably fit to a wearer.

Figure 4:
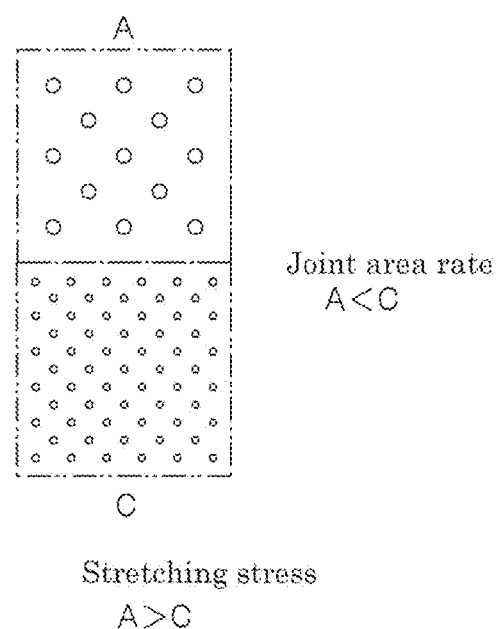
FIG. 4 is an outline plan view of a further example configuration of domains for joints having different area rates.

With reference to FIG. 4, domains for joints having different joint area rates are disposed in the up-down direction (front-back direction of the disposable diaper).

Figure 5:
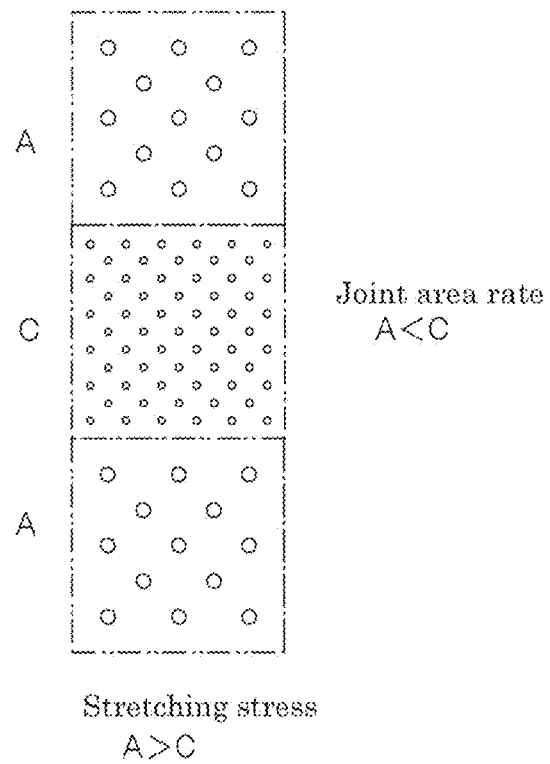
FIG. 5 is an outline plan view of a still further example configuration of domains for joints having different area rates.
Figure 6:
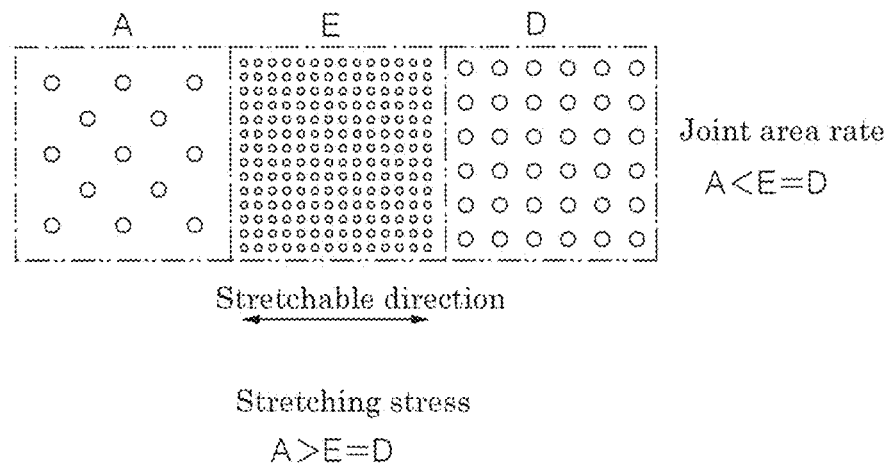
FIG. 6 is an outline plan view of a yet further example configuration of domains for joints having different area rates.

Also available are a configuration of domains for joints with different joint area rates are disposed in t up-down direction as shown in FIG. 5, and a configuration of domains for joints with different joint area rates are disposed in the transverse direction as shown in FIG. 6.

In the present invention, the difference in joint area rate can be achieved by varying the density or area of the joints.

In order to clarify this description, domain E in FIG. 6 contains a large number of small joints such that the total joint area has the same joint area as that of domain D. The relation of the joint area is determined to be domain A<domain E=domain D, so that the stretching stress has the relation: domain A>domain E=domain D.

Although the elastic film in the present invention may be stretchable only in the width direction, a biaxially stretchable film is preferred that can be stretched also in the perpendicular direction.

The physical properties, such as thickness, material, stress-strain characteristics, and melting point of the elastic film can be appropriately selected. With reference to FIG. 10, optimization of the relation between the ultrasonic energy for melting the elastic film and the stretch rate of the elastic film during production of a stretchable sheet allows the through holes 31 to be formed around the joints 40. Since the nonwoven fabric of the first sheet layer 21 and the second sheet layer 22 has air permeability, formation of the through holes 31 achieves air permeability across the stretchable sheet. In the case that the sheet is used for the disposable diaper ventrodorsally, the sheet becomes to have high air permeability.

Although the reason for formation of the breathable through holes 31 is not necessarily clear, it is presumed as follows: The elastic film 30 is melted by ultrasonic energy and the joints 40 are thinned by compressing force of the protrusions 60a on the anvil roll 60. The elastic film 30 is also thinned while the surroundings of the joints 40 reach their rupture strength. The stretching stress applied to the stretched elastic film 3 initiates the rupture of the film and the film contracts to a balanced position to form the through holes.

Figure 12:
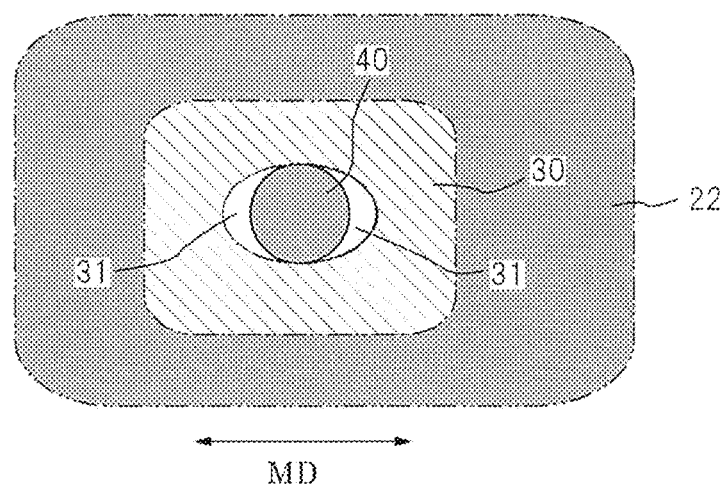
FIG. 12 is a plan view illustrating example formation of a through hole.

FIG. 12 is a schematic plan view illustrating example formation of circular through holes 31. Substantially crescent through holes 31 are both sides of the joints 40 in the machine direction (stretchable direction).

Figure 13:
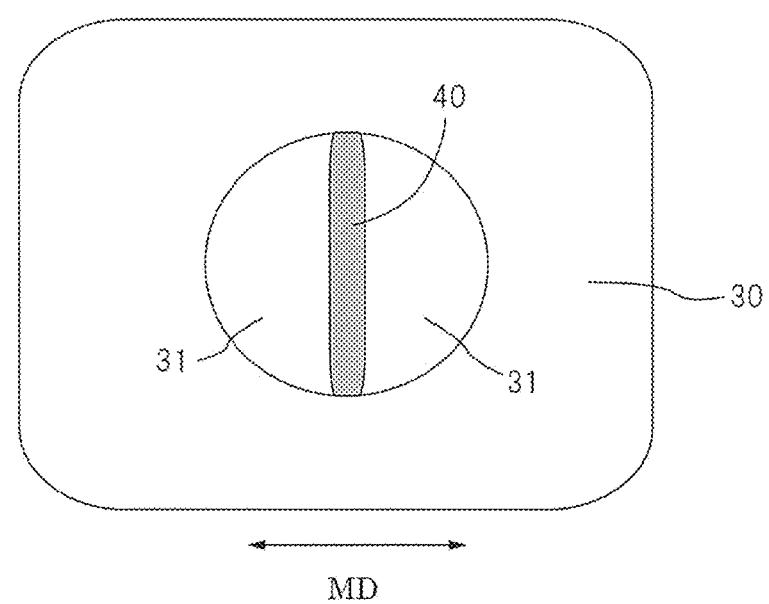
FIG. 13 is a plan view illustrating other example formation of a through hole.

The joints may have an oblong shape in the cross direction (CD) perpendicular to the machine or stretchable direction. In this case, as shown in FIG. 13, large semicircular through holes 31, for example, can be formed. This configuration is suitable for an enhancement in air permeability.

Figure 14:
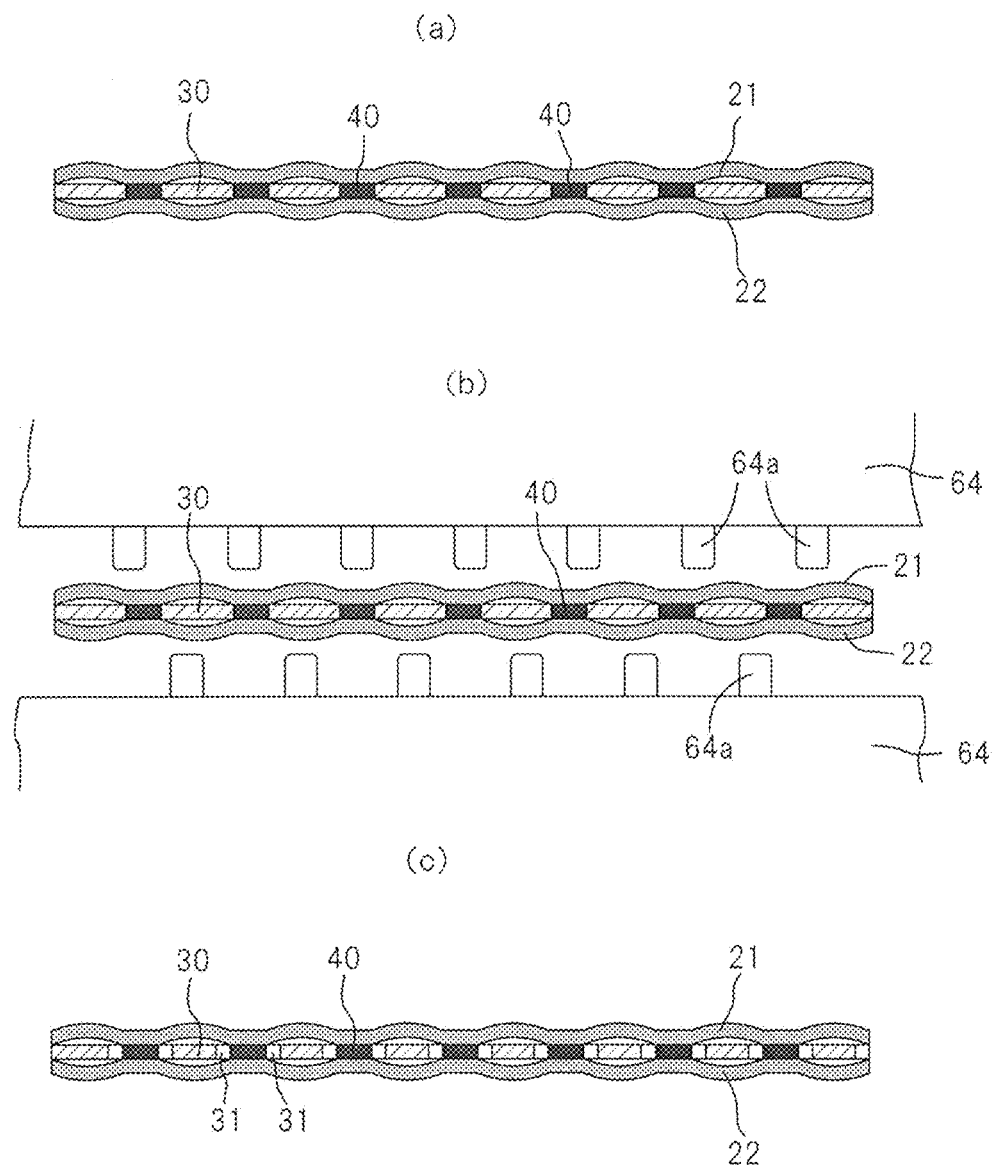
FIG. 14 illustrates formation of through holes by another process.

It is not essential that all the joints have through holes 31. In the case that the through holes 31 are certainly formed or large through holes are formed, a means shown in FIG. 14 can be employed.

The stretchable sheet having joints 40 is introduced between a pair of rolls 64 having line or dot protrusions as shown in FIG. 14(b) while each protrusion 64a of one of the rolls 64 is engaged into a space between adjacent protrusions 64a, 64a of the other roll 64, so that deformation force is applied to the stretchable sheet to form the through holes 31.

(Application to Underpants-Type Disposable Diaper)

The resulting stretchable sheet can be applied to disposable diapers. An application of the stretchable sheet to an underpants-type disposable diaper will now be described.

FIGS. 15 to 20 illustrate an underpants-type disposable diaper. This underpants-type disposable diaper (hereinafter simply referred to as diaper) includes an outer member 20 composed of a front body Fr and a back body Ba and an inner member 10 that is fixed in a unified manner to the inner face of the outer member 20. The inner member includes a liquid-pervious front face sheet 11, a liquid-impervious back face sheet 12, and an absorber 13 disposed therebetween. In manufacture of the underpants-type disposable diaper, after the back face of the inner member 10 is bonded to the inner or upper face of the outer member 20 by any bonding means, such as hot melt adhesion (shaded area 10B in FIG. 21), the inner member 10 and the outer member 20 are folded at boundary between the front body Fr and the back body Ba, i.e., in the center in the front-back direction or longitudinal direction, and both side edges of the folded body are bonded by thermal welding or hot melt adhesion to form side seal portions 26. An underpants-type disposable diaper having a waist opening and a pair of right and left leg openings is thereby produced.

(Example Structure of Inner Member)

Figure 18:
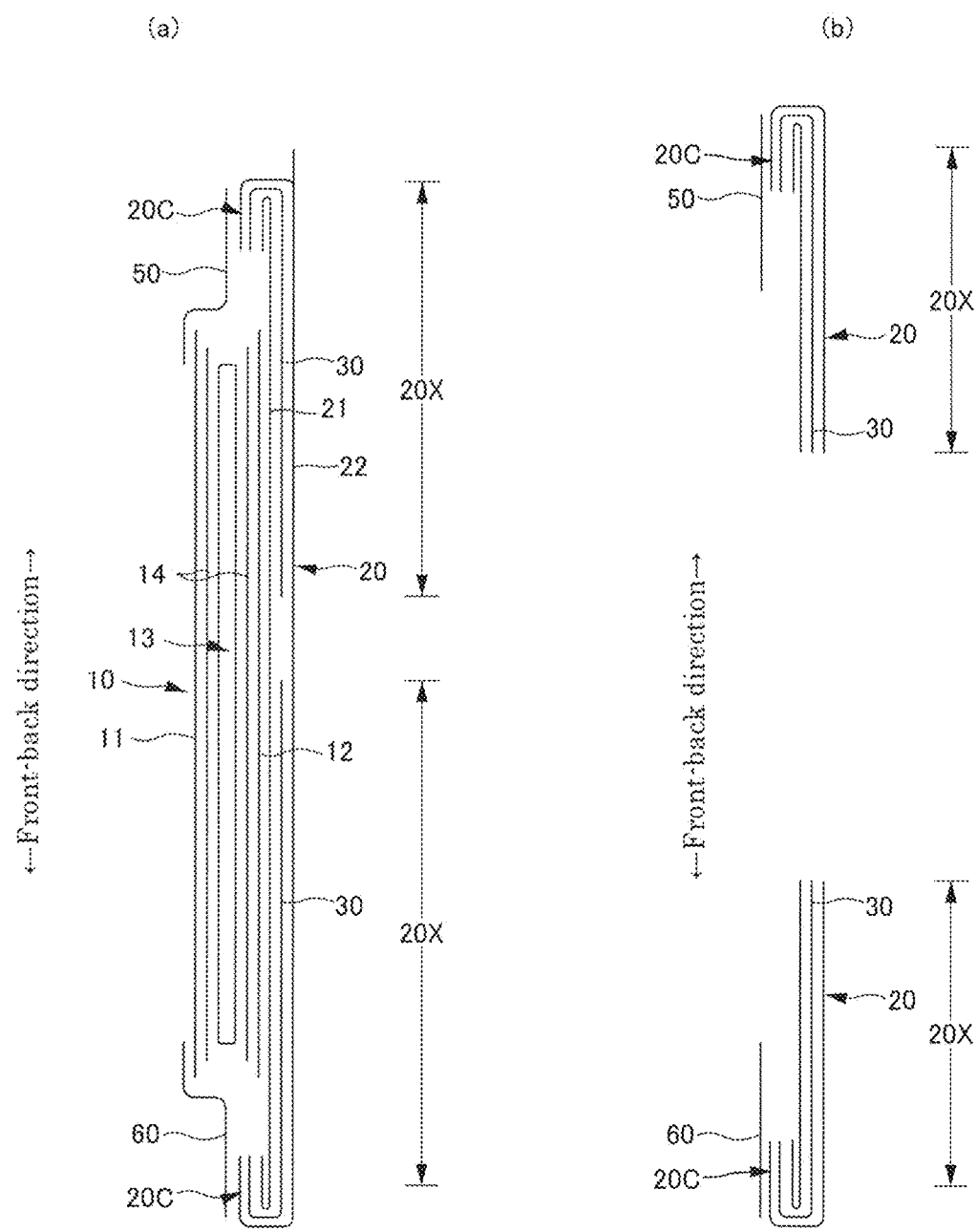
FIGS. 18(a) and 18(b), respectively, are 18a-18a and 18b-18b cross-sectional views of FIG. 16.
Figure 19:
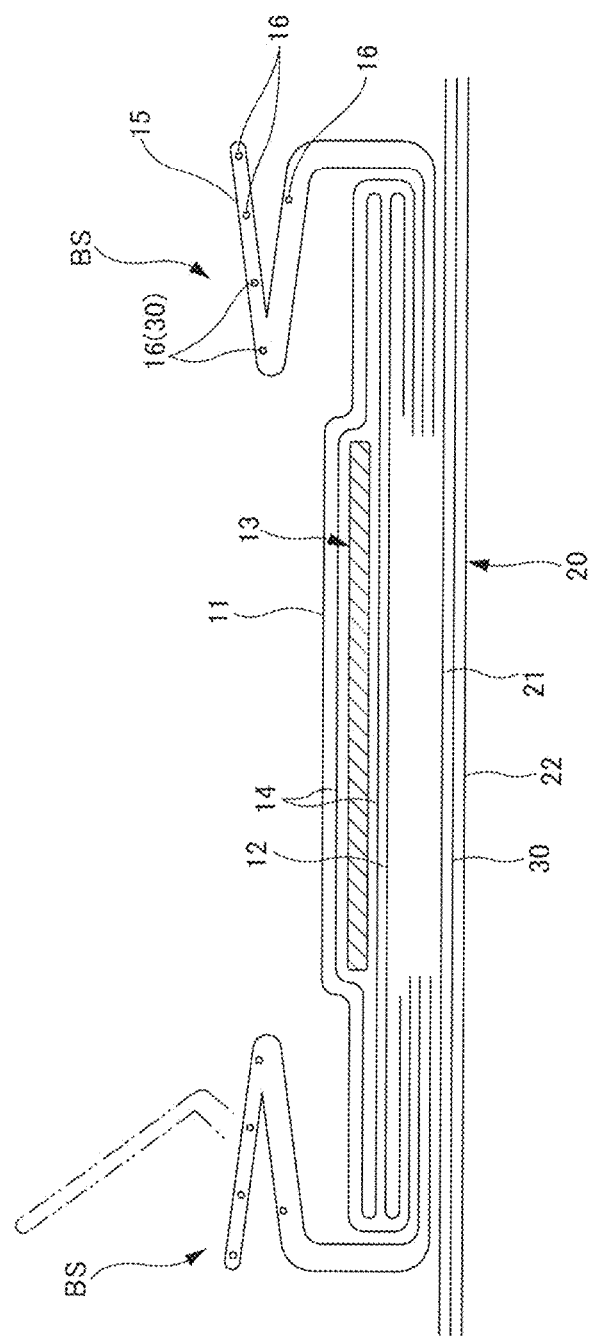
FIG. 19 is a 19-19 cross-sectional view of FIG. 16.
Figure 20:
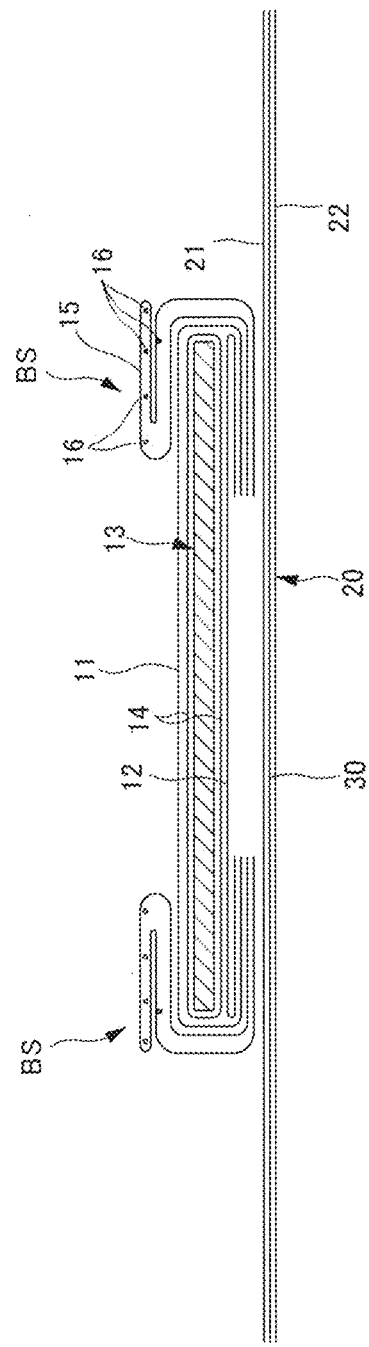
FIG. 20 is a 20-20 cross-sectional view of FIG. 16.
Figure 21:
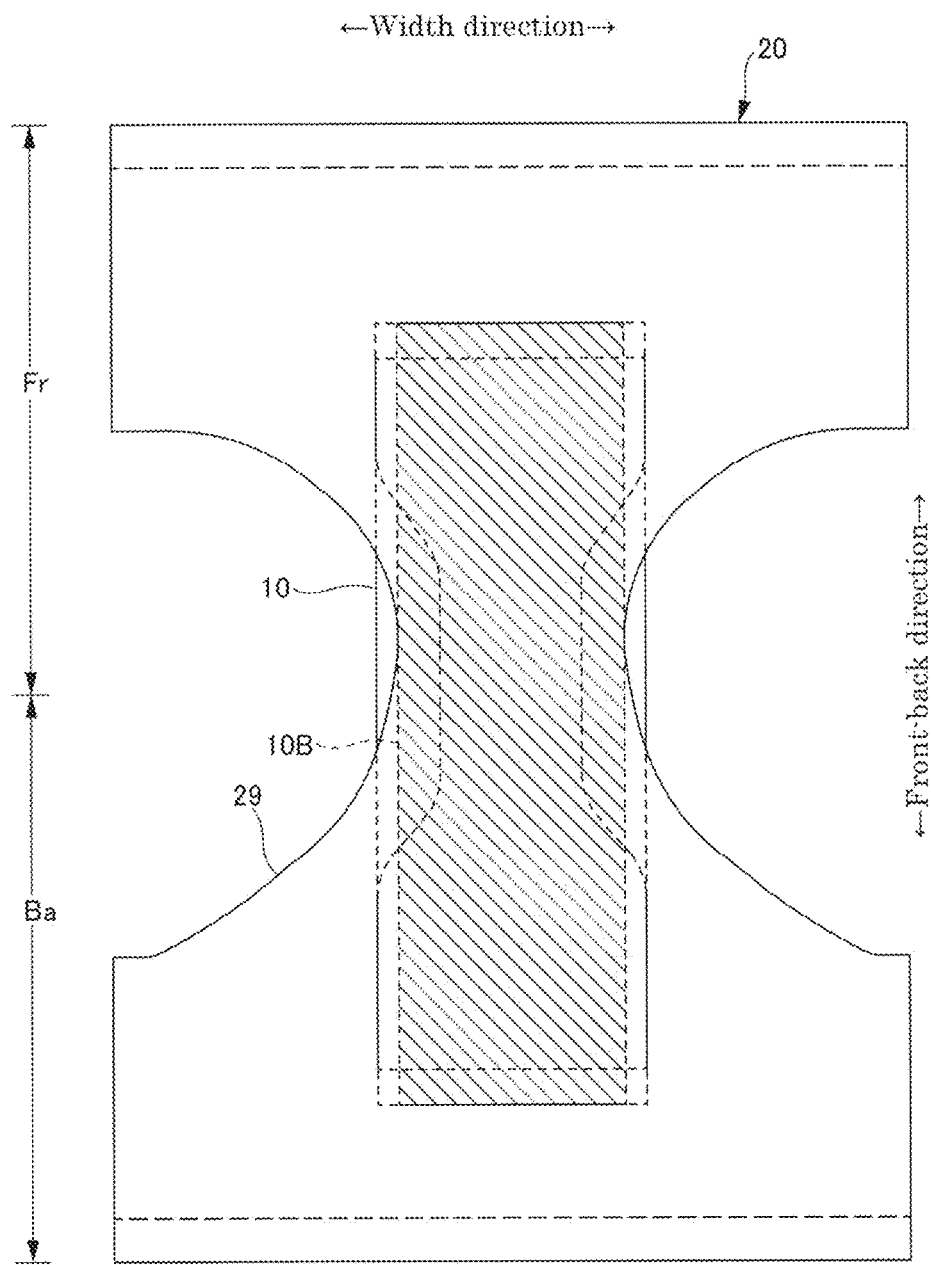
FIG. 21 is a plan view illustrating only the main portion of an underpants-type disposable diaper in a completely unfolded state.

With reference to FIGS. 18 to 20, the inner member 10 includes a liquid-pervious front face sheet 11 composed of, for example, nonwoven fabric, a liquid-impervious back face sheet 12 composed of, for example, polyethylene, and the absorber 13 disposed therebetween to absorb and retain excretory fluid passing through the front face sheet 11. The inner member 10 may have any planar shape and typically has a substantially rectangular shape as shown in the drawing.

The liquid-pervious front face sheet 11 that covers a front face (to come into contact with the skin) of the absorber 13 is preferably composed of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and copra; and natural fibers, such as cotton. The nonwoven fabric can be produced by any process, for example, spunlacing, spunbonding, thermal bonding, melt blowing, or needle punching. Among these processes, preferred are spunlacing in view of softness and drape characteristics and thermal bonding in view of bulky soft products. A large number of through holes formed in the liquid-pervious front face sheet 11 facilitates absorption of urine and achieves dry touch characteristics. The liquid-pervious front face sheet 11 extends around the side edges of the absorber 13 and extends to the back face of the absorber 13.

The liquid-impervious back face sheet 12 covering the back face (not in contact with skin) of the absorber 13 is composed of a liquid-impervious plastic sheet, for example, polyethylene sheet or polypropylene sheet. Recently, permeable films have been preferably used in view of preventing stuffiness. This water-block permeable sheet is a microporous sheet prepared through melt-kneading an olefin resin, for example, polyethylene resin or polypropylene resin, and inorganic filler, forming a sheet with the kneaded materials, and then uniaxially or biaxially elongating the sheet.

The absorber 13 may be composed of a well-known basic component, for example, an accumulated body of pulp fibers, an assembly of filaments, composed of, for example, cellulose acetate, or nonwoven fabric, and the absorber 13 may include as necessary high-absorbent polymer mixed or fixed to the basic component. The absorber 13 may be wrapped with a liquid-pervious and liquid-retainable package sheet 14, such as crepe paper for shape and polymer retention, if necessary.

The absorber 13 has a substantially hourglass shape in which the crotch portion has a narrower part 13N with a width narrower than those of the front and back portions of the absorber 13. Alternatively, the absorber may have any other shape, for example, a rectangular shape. The narrower part 13N may have any dimensions. The length of the narrower part 13N in the front-back direction may be approximately 20% to approximately 50% of the entire length of the diaper, and the width of the narrowest portion may be approximately 40% to approximately 60% of the entire width of the absorber 13. If the inner member 10 has a substantially rectangular planar shape in the case of the absorber 13 with such a narrower part 13N, the inner member 10 has portions free of the absorber 13 according to the narrower part 13N of the absorber 13.

The inner member 10 has three-dimensional gathers BS fitting to legs of a wearer on the two sides. With reference to FIGS. 19 and 20, the three-dimensional gathers BS are each composed of a gather nonwoven fabric 15 in the form of a duplicated sheet that consists of a fixed section fixed to the side of the back face of the inner member, a main unit section extending from the fixed section through the side of the inner member to the side of the front face of the inner member, lying down sections formed by fixing the front end and back end of the main unit section in a lying down state to the side of the front surface of the inner member, and a free section formed in an un-fixed state between the lying down sections.

Elongated gather elastic members 16 are disposed in each duplicate sheet, for example, at the tip of the free section. As illustrated with a two-dotted line in FIG. 19, the free section of the gather elastic member 16 is erected by elastic stretching force into the three-dimensional gather BS.

The liquid-impervious back face sheet 12 and the liquid-pervious front face sheet 11 are turned at the two sides of the absorber 13 in the width direction toward the back face of the absorber 13. The liquid-impervious back face sheet 12 is preferably opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 16 may be composed of commodity materials, for example, styrene rubber, olefin rubber, urethane rubber, ester rubber, polyurethanes, polyethylene, polystyrene, styrene-butadiene, silicones, and polyester. The gather elastic members 16 preferably have a fineness of 925 dtex or less and are disposed under a tension of 150% to 350% at an interval of 7.0 mm or less to be hidden from outside view. The gather elastic member 16 may have a string shape shown in the drawing or a tape shape with an appropriate width.

Like the liquid-pervious front face sheet 11, the gather nonwoven fabric 15 may be composed of any fibers. Examples of the raw fibers include synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. The gather nonwoven fabric 15 is preferably a water-repellent nonwoven fabric coated with a water repellent agent, for example, a silicone-based agent, a paraffin-metallic agent, or an alkyl chromic chloride agent to prevent penetration of urine, to prevent diaper rash, and to enhance feeling to skin (dryness).

(Example Structure of Outer Member)

With reference to FIGS. 16 to 21, the outer member 20 includes the elastic film 30 disposed between the first sheet layer 21 and the second sheet layer 22 to impart elasticity in the width direction. The entire outer member 20 has a planar shape of a substantially hourglass having narrowed portions along leg lines 29 at the two sides and at the middle of the outer member 20. Alternatively, the outer member 20 may be divided into two front and back pieces that are separated from each other at a crotch portion.

Figure 16:
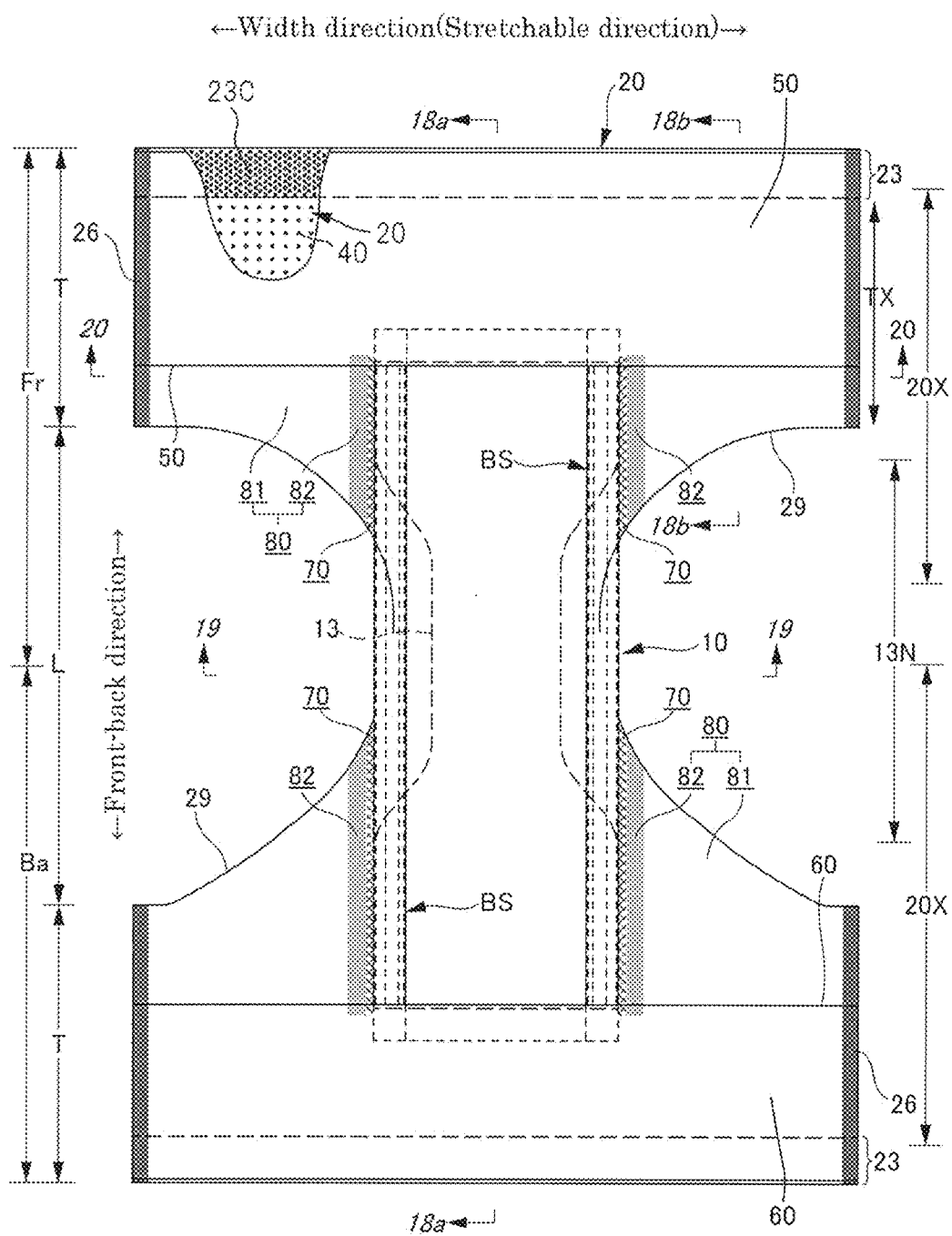
FIG. 16 is an inner plan view of an underpants-type disposable diaper in a completely unfolded state.

In more detail, in the outer member 20 illustrated in FIG. 16, in the torso regions T defined as vertical ranges with the side seal portions 26 at which the front body Fr is bonded to the back body Ba, the stretching stress in the waist portion 23 is greater than that in the underpart portion TX. This configuration can generate a stretching force appropriately tightening the waist. The following relation holds: torso region T=waist portion 23+underpart portion TX.

The waist portion 23 is composed of a turn-up portion 20C prepared by turning up the extension of the outer member 20 including the elastic film toward the internal surface side.

The first sheet layer 21 and the second sheet layer 22 may be composed of any sheet members, preferably nonwoven fabrics in view of air permeability and softness. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and copra; natural fibers, such as cotton; and blend or conjugate fibers composed of two or more of these fibers. The nonwoven fabric may be prepared by any process. Examples of such a process include well-known processes, such as spunlacing, spunbonding, thermal bonding, melt blowing, needle punching, air-through processes, and point bonding. The nonwoven fabric preferably has a basis weight of approximately 10 to approximately 25 g/m$^2$. The first sheet layer 21 and the second sheet layer 22 may be composed of a pair of facing layers prepared by turning up a single sheet that is partially or entirely turned up.

In this embodiment shown in FIG. 16, the laminate stretchable structures 20X of the above mentioned stretchable sheet are formed in the torso region T of the front body Fr, the torso region T of the back body Ba, and an intermediate layer L in the outer member 20. In this embodiment, the torso region T, the torso region T of the back body Ba, and part of the intermediate region L define the "stretchable region" of the present invention. As shown in FIG. 18(a), the central portion in the front-back direction of the intermediate region L is a non-stretchable region because no elastic film 30 is present in this region.

In the region of the stretchable structures 20X of the outer member 20, the non-stretchable region 70 is formed in an intermediate portion in the width direction, which includes parts of the outer member 20 overlapping with the absorber 13 (the non-stretchable region 70 may entirely or partly overlap with the absorber 13 and preferably should contain the substantially entire fixed portion 10B of the inner member) as well as the stretchable regions 80, which are stretchable in the width direction, extend to the side seal portions 26 in the width direction. The elastic film 30 is disposed between the first sheet layer 21 and the second sheet layer 22 over the entire stretchable regions 80 and the non-stretchable region 70, and the first sheet layer 21 and second sheet layer 22 are bonded at a large number of joints 40 arrayed in the stretchable direction (width direction) and the perpendicular direction (front-back direction) at predetermined intervals (via the through holes 31 formed in the elastic film 30 in the embodiment shown in the drawing) while the elastic film 30 is being stretched in the width direction.

Basically, as the area rate of the joints 40 increases in the laminated stretchable structure 20X, portions contracted by the elastic film 30, of the first sheet layer 21 and the second sheet layer 22 decrease, and the elongation at elastic limit is likely to decrease. Accordingly, the area rate of the openings of the through holes 31 in the elastic film 30 increases, and thus the proportion of the elastic film 30 continuing in the stretchable direction decreases in a direction perpendicular to the stretchable direction. Accordingly, the contraction force to be generated in a stretched state decreases, and the risk of rupture of the elastic film 30 increases.

In view of such characteristics, the area rate of the joints 40 in the non-stretchable region 70 is determined to be larger than that in the stretchable regions 80, such that the elongation at elastic limit in the stretchable direction is 130% or less (preferably 120% or less, more preferably 100%). In contrast, the area rate of the joints 40 in the stretchable regions 80 is determined to be smaller than that in the non-stretchable region 70, such that the elongation at elastic limit in the stretchable direction is 200% or higher (preferably 265 to 295%). The term "elongation at elastic limit" means elongation in the state that the first sheet layer and the second sheet layer are completely stretched and is expressed in percentage relative to the natural-length 100% at elongation limit.

In the stretchable region 80, when the elastic film 30 is in the natural-length state, as illustrated in FIG. 9, the first sheet layer 21 and the second sheet layer 22 are raised apart from each other, forming contracted wrinkles 25 extending in a direction intersecting with the stretchable direction. When the elastic film 30 is stretched to an extent in the width direction, as illustrated in FIG. 8, the contracted wrinkles 25 are still remain although the bulged height is small. The sampled photographs shown in FIGS. 24 to 26 also show the states of the contracted wrinkles 25 at the worn state and the natural-length state.

Figure 24:
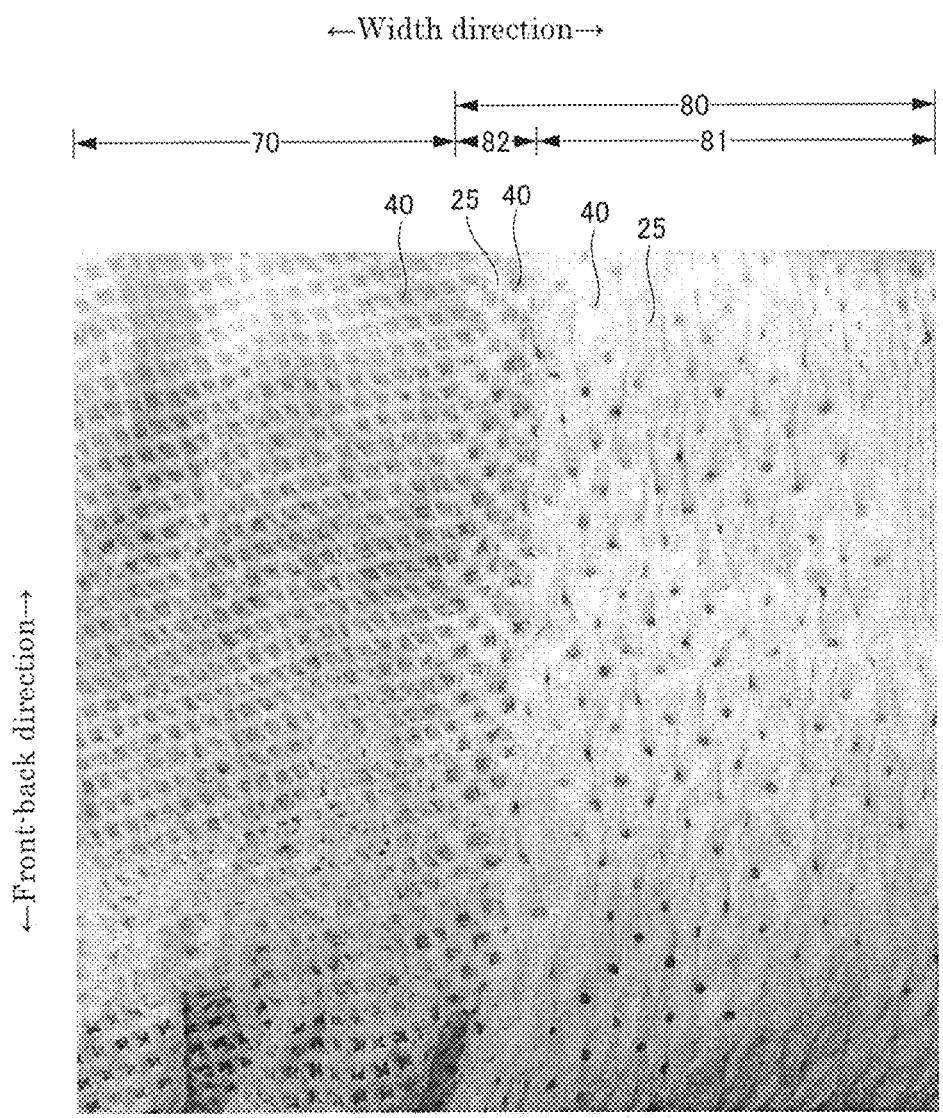
FIG. 24 is a photograph of a sample in a natural-length state.
Figure 25:
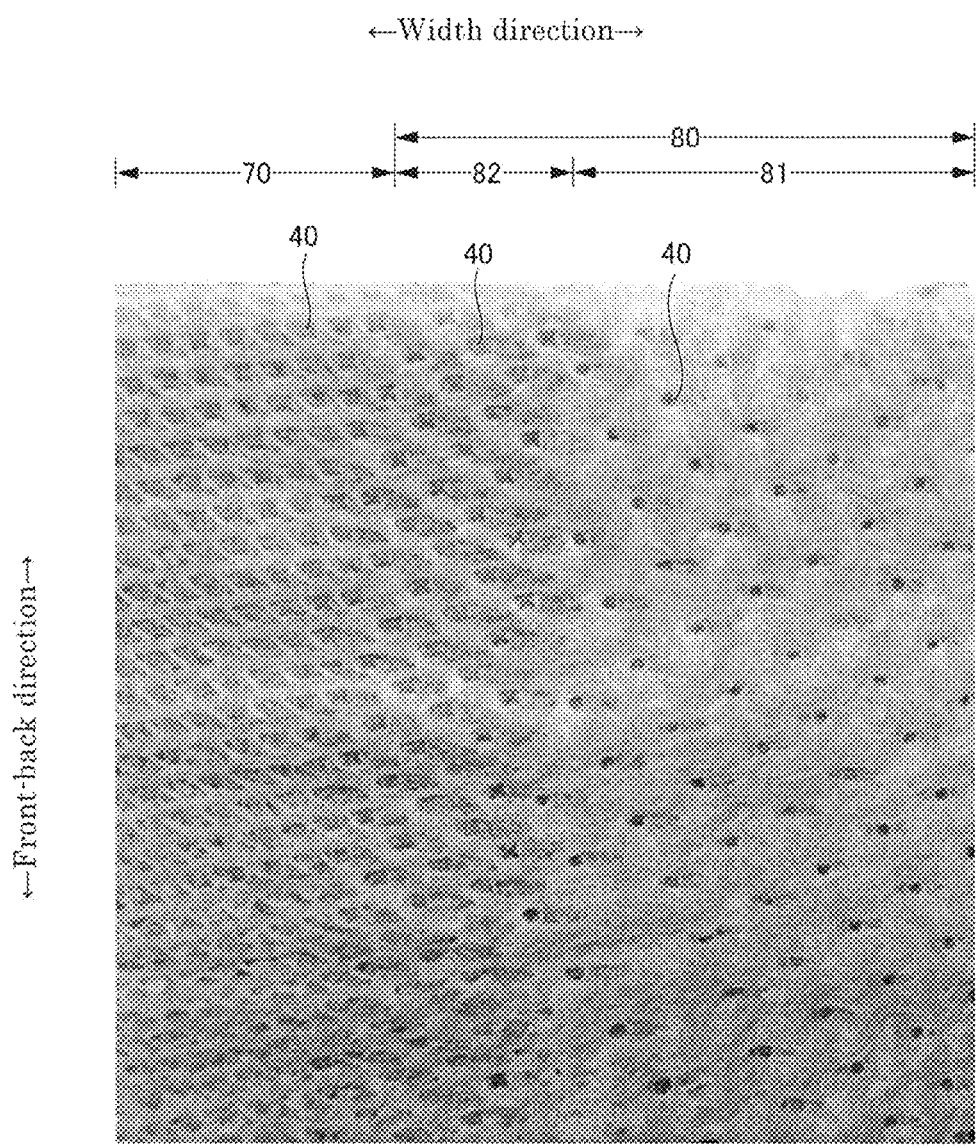
FIG. 25 is a photograph of a sample in a stretched state.
Figure 26:
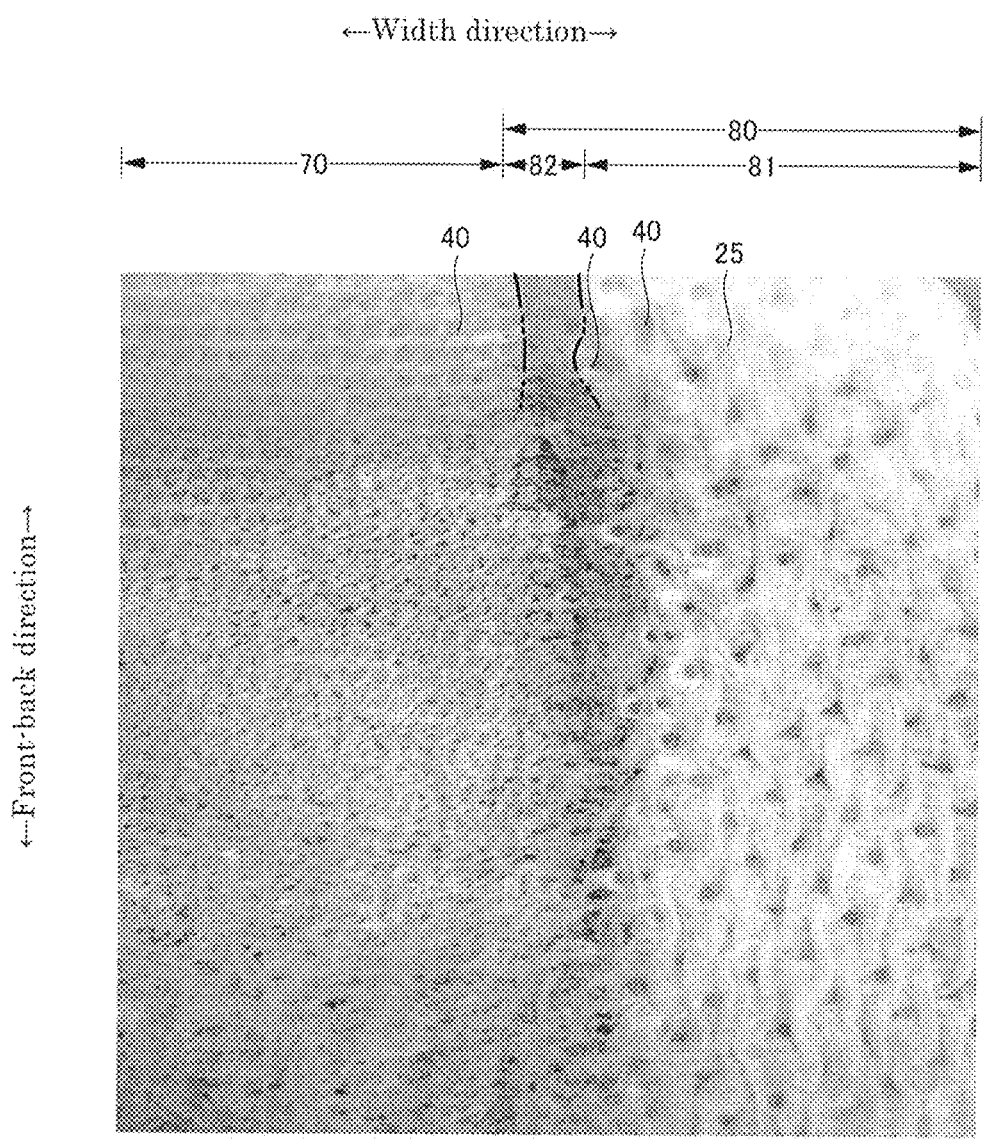
FIG. 26 is a photograph of a sample in a natural-length state after the elastic film is ruptured.
Figure 27:
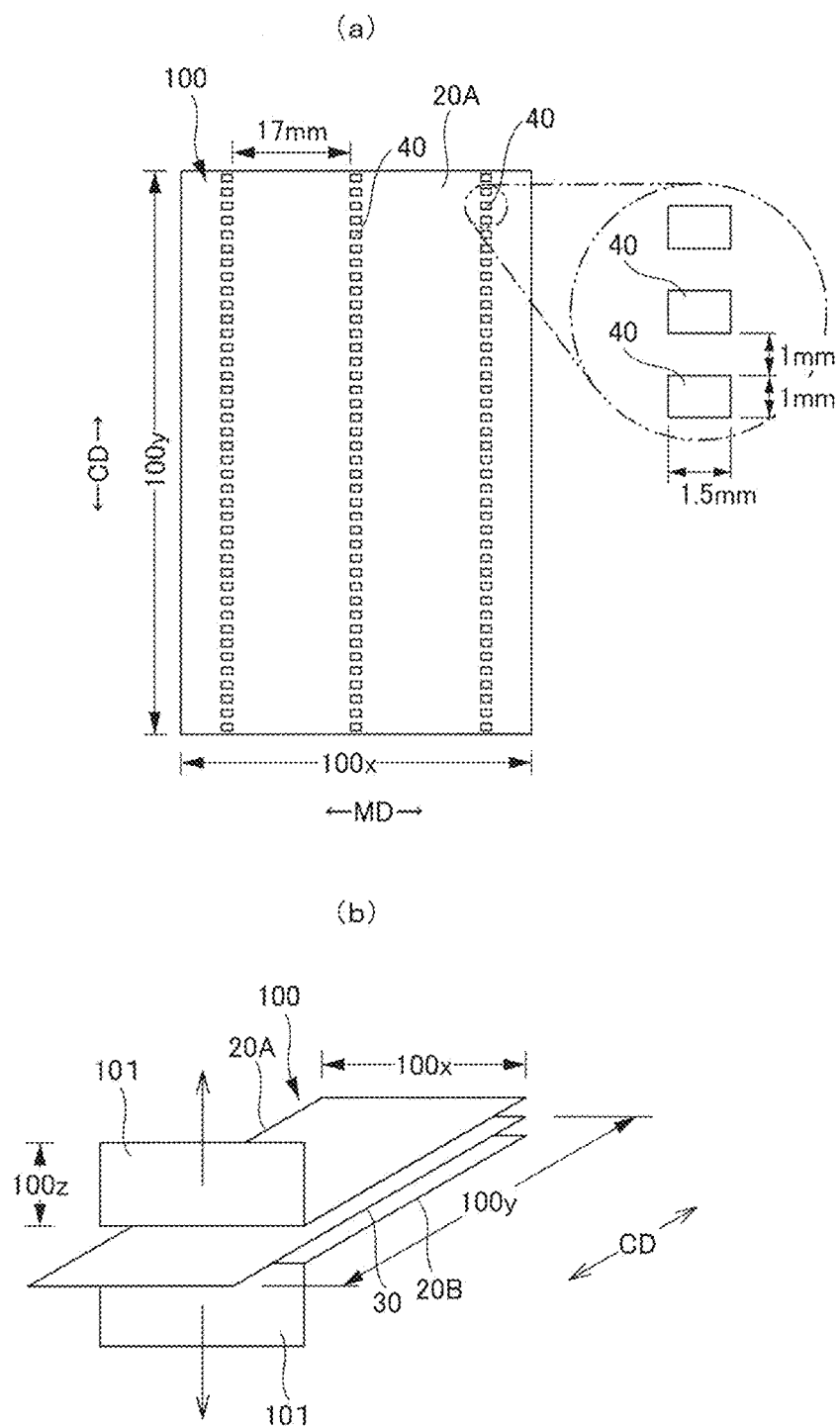
FIG. 27 is a schematic view illustrating a peel test.

As shown in the sampled photographs of FIGS. 24 to 26, although streaky protrusions or significantly fine wrinkles are formed between joints 40 in the non-stretchable region 70, the elasticity is substantially lost due to a significantly high area rate of joints 40.

Figure 17:
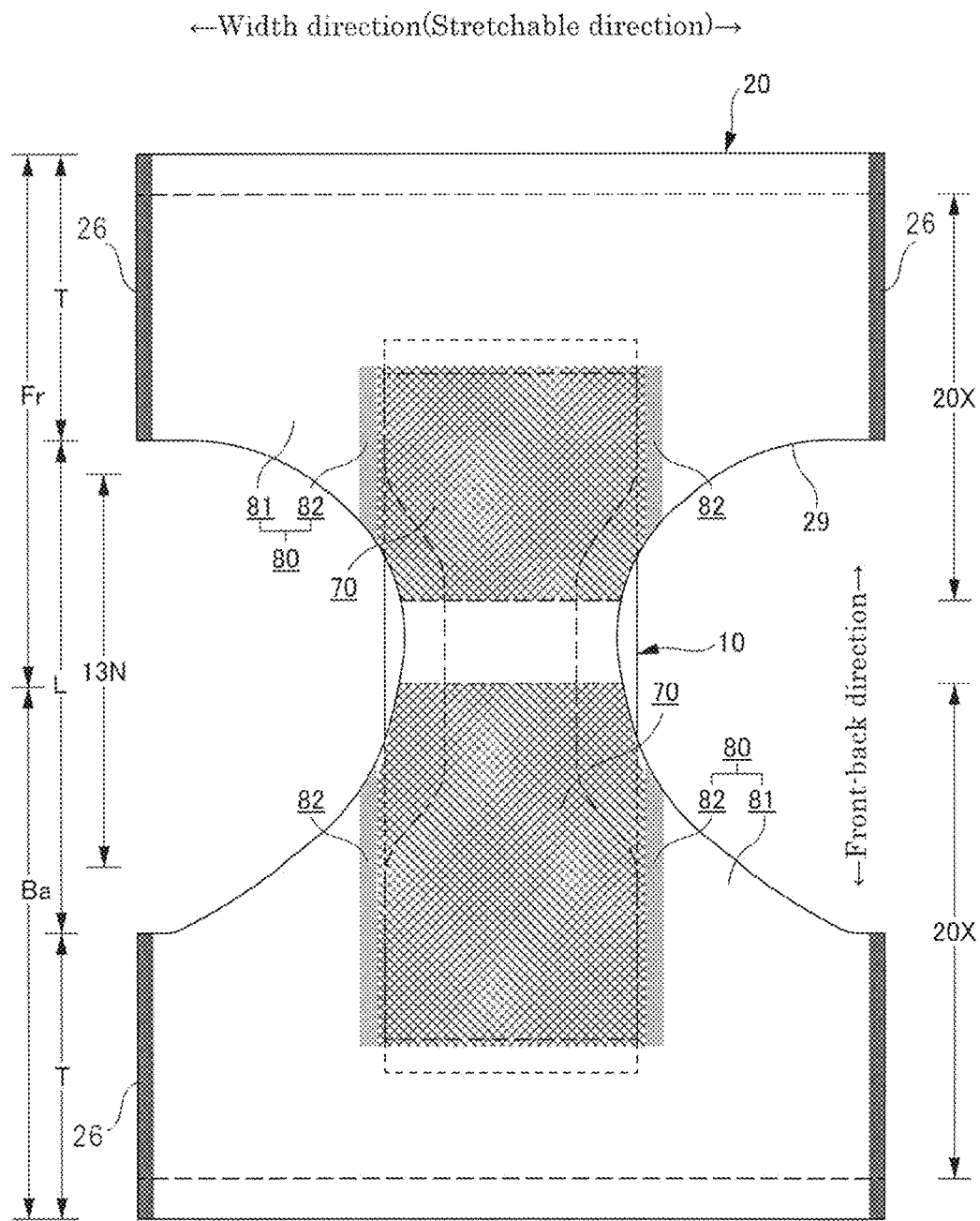
FIG. 17 is an outer plan view of an underpants-type disposable diaper in a completely unfolded state.
Figure 22:
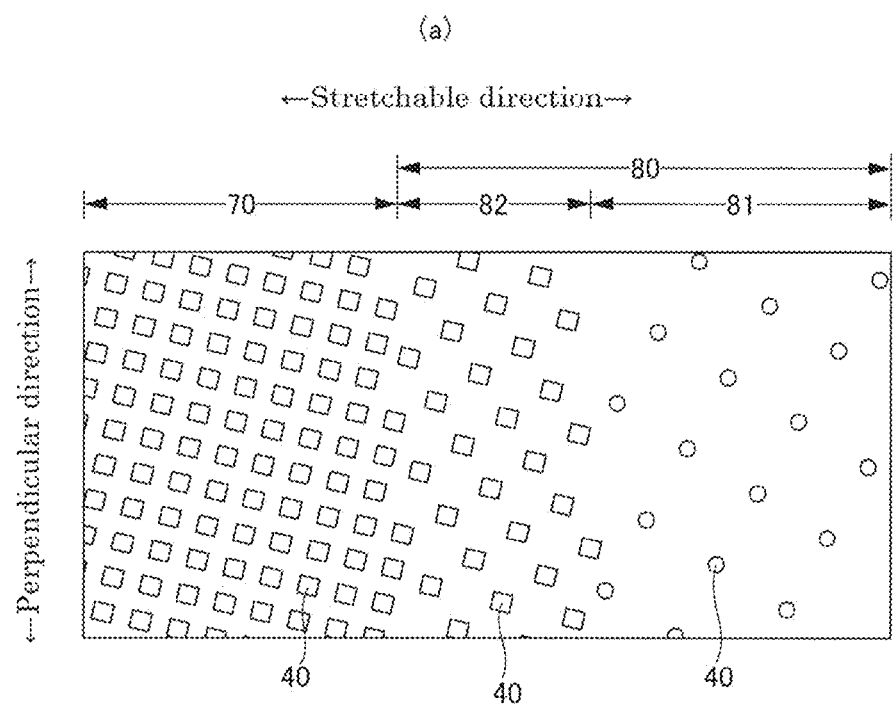
FIG. 22 is a plan view illustrating joint geometry in a torso region of an outer member stretched to some extent in the width direction.
Figure 22:
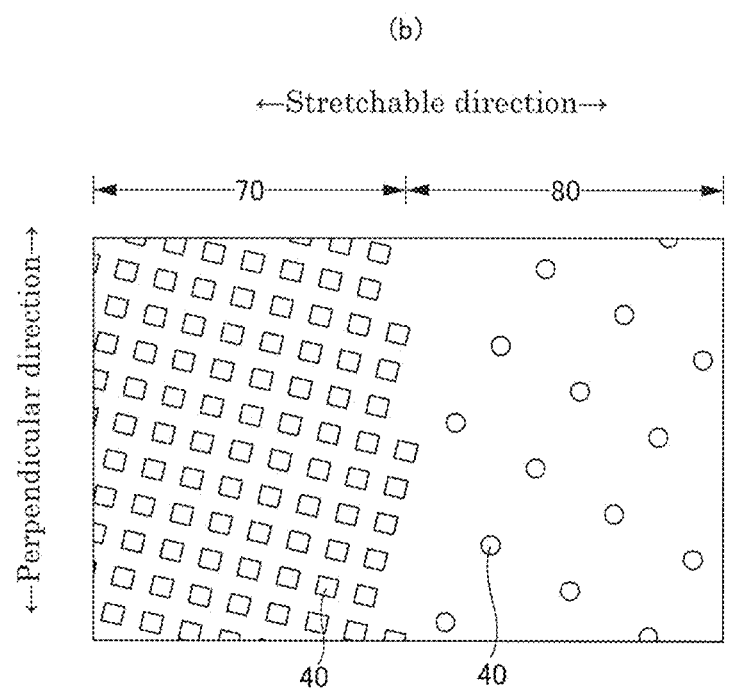

As shown in FIGS. 16, 17 and 22(a), the ends of the stretchable regions 80 adjacent to the non-stretchable region 70, are buffer stretchable sections 82 each having an area rate of joints 40 lower than that of a main stretchable section 81 not including the buffer stretchable section.

Alternatively, no buffer stretchable section 82 may be provided as shown in FIG. 22(b).

Each of the joints 40 and through holes 31 may have any shape, for example, circular, oval, polygonal, such as rectangular (including in the shape of rod and with rounded corners), star-shaped, or cloud-shaped. The size of each joint 40 may be appropriately determined. At an excessively large size, the hardness of the joints 40 significantly affects the touch, whereas at an excessively small size, the bonded area is too small to certainly bond the layers. Each of the joints 40 preferably has an area of approximately 0.14 to 3.5 mm$^2$, in usual cases. Each of the through holes 31 should have an opening area larger than that of the corresponding joint 40 such that the joint 40 is formed within the through hole 31. The through hole 31 preferably has an opening area of approximately 1 to 1.5 times the area of the joint 40.

In general, the preferred areas and area rate of the joints 40 in each field are as follows.

<Non-Stretchable Region 70>

Area of joint 40: 0.14 to 3.5 mm$^2$ (in particular, 0.25 to 1.0 mm$^2$)

Area rate of joints 40: 16 to 45% (in particular, 25 to 45%)

<Main Stretchable Section 81>

Area of joint 40: 0.14 to 3.5 mm$^2$ (in particular, 0.14 to 1.0 mm$^2$)

Area rate of joints 40: 1.8 to 19.1% (in particular, 1.8 to 10.6%)

<Buffer Stretchable Section 82>

Area of joint 40: 0.14 to 3.5 mm$^2$ (in particular, 0.25 to 1.0 mm$^2$)

Area rate of joints 40: 8 to 22.5% (in particular, 12.5 to 22.5%).

Figure 23:
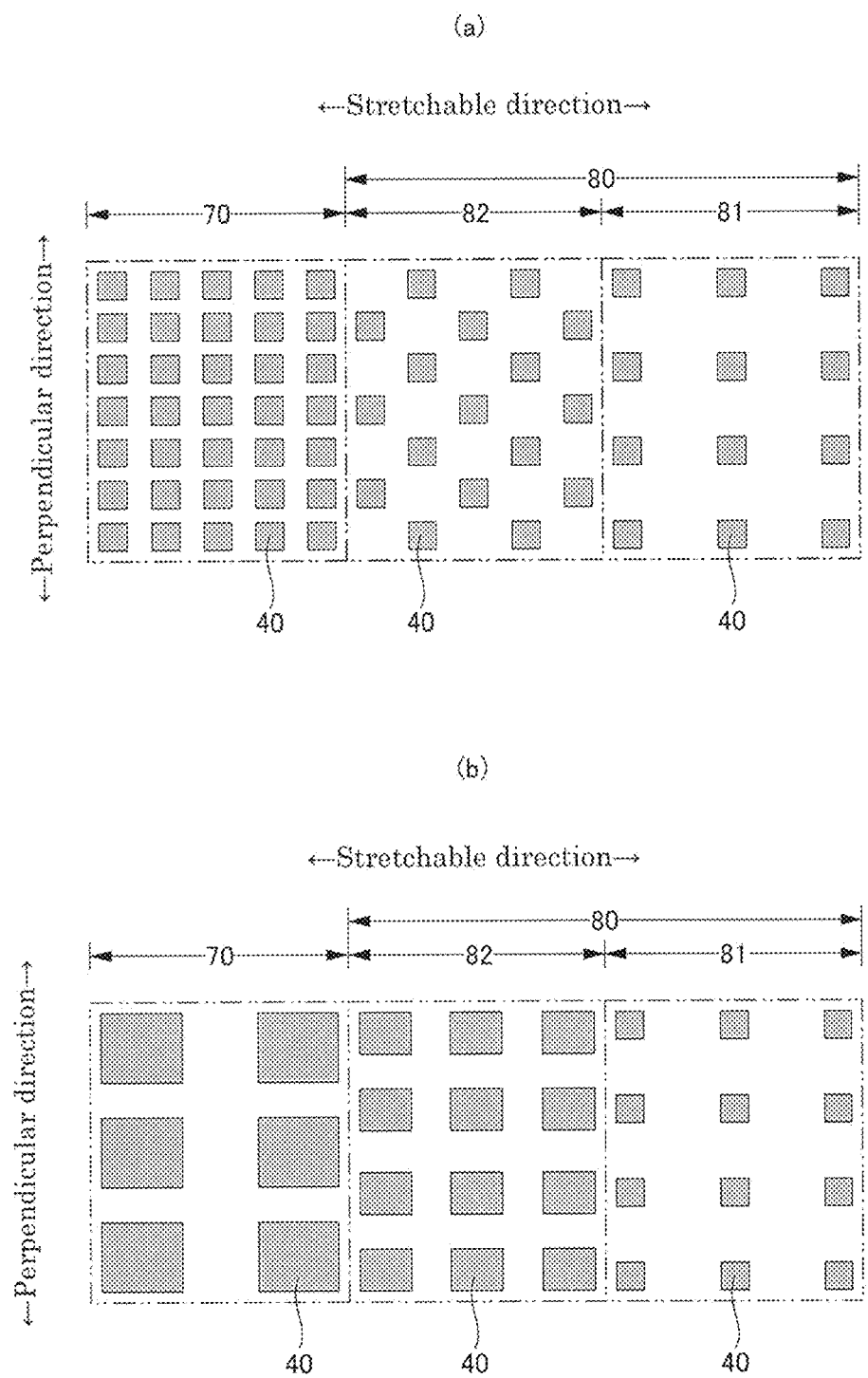
FIG. 23 a plan view illustrating example joint geometry of another embodiment.

To produce three fields (i.e., the non-stretchable region 70, the main stretchable section 81, and the buffer stretchable section 82) having different area rates, the number of the joints 40 per unit area may be varied, as illustrated in FIG. 23(a), or the area of each joint 40 may be varied, as illustrated in FIG. 23(b). In the former case, the areas of the joints 40 may be the same between two or more fields of the non-stretchable region 70, the main stretchable section 81, and the buffer stretchable section 82, or may be different among all the fields. In the latter case, the number of the joints 40 per unit area may the same between two or more fields of the non-stretchable region 70, the main stretchable section 81, and the buffer stretchable section 82, or may be different among all the fields.

Figure 28:
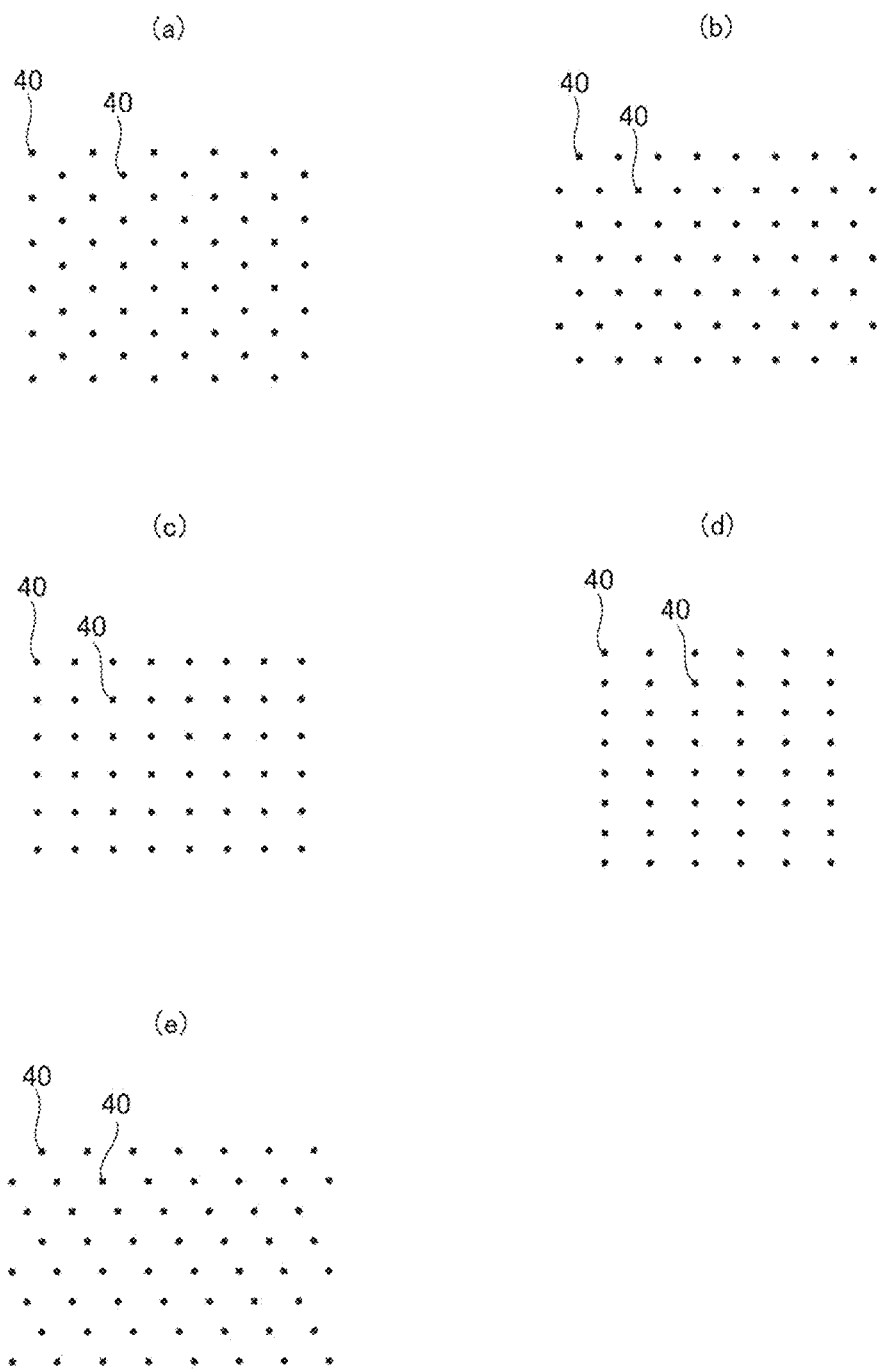
FIG. 28 includes plan views illustrating various geometries of joints.

The planar geometries of the joints 40 and through holes 31 can be appropriately determined. Regularly repeated geometry is preferred. Examples of the regularly repeated geometry include rhombic lattice shown in FIG. 28(a), hexagonal lattice shown in FIG. 28(b) (referred to as staggered), square lattice shown in FIG. 28(c), rectangular lattice shown in FIG. 28(d), and parallelotope shown in FIG. 28(e) (a group of diagonal parallel arrays intersects another group of diagonal parallel arrays as shown in the drawing) (including arrays tilted by less than degrees to the stretchable direction); and regularly repeated groups of joints 40 (the geometry in each group may be regular or irregular, in other words, may be a pattern or a letter, for example). The geometries of the joints 40 and through holes 31 may be the same or different between the main stretchable section 81, buffer stretchable section 82, and non-stretchable region 70.

The elastic film 30 may be composed of any resin film having elasticity. Usable examples of the resin film include styrene elastomer resin film, olefin elastomer resin film, polyester elastomer resin film, polyamide elastomer resin film, polyurethane elastomer resin film, and blends thereof. The material may be shaped into a film through extrusion such as a T-die extrusion or an inflation extrusion. The elastic film 30 may have no pore or may have a large number of pores or slit for aeration. In a preferred embodiment, the elastic film 30 has a tensile strength in the stretchable direction in the range of 8 to 25 N/35 mm, a tensile strength in the direction perpendicular to the stretchable direction in the range of 5 to 20 N/35 mm, a tensile elongation in the stretchable direction in the range of 450 to 1050%, and a tensile elongation in the direction perpendicular to the stretchable direction in the range of 450% to 1400%. The tensile strength and the tensile elongation at break are measured at an initial chuck interval of 50 mm and a speed of testing of 300 mm/min with a tensile tester (for example, AOUTGRAPHAGS-G100N available from SHIMADZU) in accordance with JIS K7127:1999 "Plastics—Determination of tensile properties", except that the test piece is a rectangle with a width of 35 mm and a length of 80 mm. The elastic film 30 may have any thickness, preferably in the range of approximately 20 to approximately 40 μm. The elastic film 30 may have any basis weight, preferably in the range of approximately 30 to approximately 45 g/m$^2$, more preferably approximately 30 to approximately 35 g/m$^2$.

The melting point of each component of the stretchable sheet of the present invention may be appropriately selected. As described above, the elastic film has a melting point of preferably in the range of 95° C. to 125° C., more preferably 100° C. to 120° C., the first sheet layer has a melting point in the range of preferably more than 125° C. to 160° C., more preferably 130° C. to 160° C., and the second sheet layer has a melting point in the range of more than 125° C. to 160° C., more preferably 130° C. to 160° C.

The ultrasonic welding temperature may be varied through selection of ultrasonic energy from the horn. Although the ultrasonic energy from the horn cannot be directly converted into temperature, the temperature ensuring stable productivity is 40° C. to 30° C. at the horn side and 38° C. to 28° C. at the anvil side where the temperature is determined with a contactless thermometer.

The observation of the bonded state under a stable operation leads the inventors to speculate that melting energy corresponding to 125° C. to 145° C., which is higher than the melting point of the elastic film, is preferably applied the elastic film from the horn side. The temperature is preferably lower than the melting points of the first sheet layer and the second sheet layer. It is preferred that the difference in melting point between the first sheet layer 21 and the elastic film 30 and between the second sheet layer 22 and elastic film 30 be approximately 10° C. to approximately 45° C.

The most suitable nonwoven fabric for the first sheet layer and the second sheet layer used ventrodorsally in a disposable diaper is spunbond nonwoven fabric.

With reference to FIG. 16, the disposable diaper has an intermediate region L between the front and rear torso regions T, T and leg portions Z (see FIG. 15) narrowed toward the center side in the width direction from the inner end points of the torso regions T in the front-back direction (in a lower side in the case of the front body Fr in FIG. 16) over the intermediate region.

Figure 15:
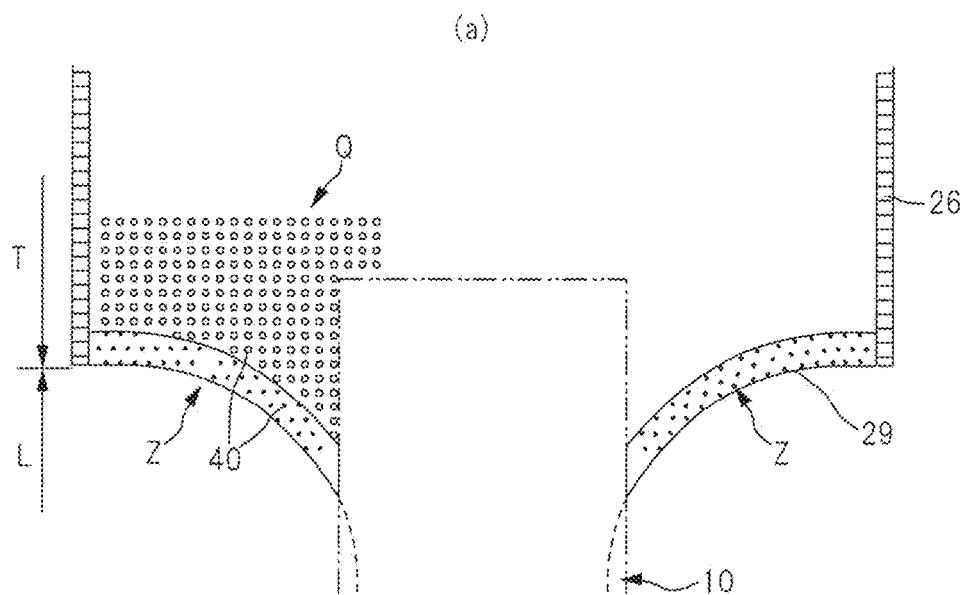
FIGS. 15(a), 15(b), and 15(c) illustrate the joint geometry in the stretchable region of leg portion.
Figure 15:
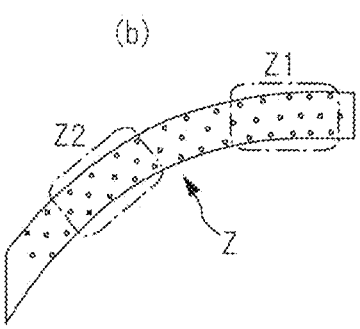
Figure 15:
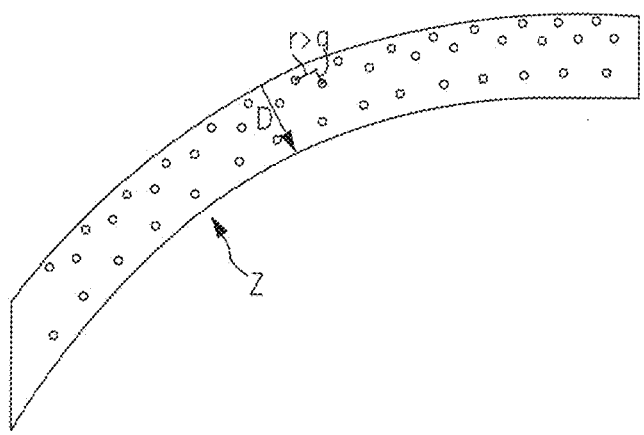

The leg portion Z is depicted in FIG. 15, but not in FIG. 16. In the present invention, at least one of the front body Fr and back body Ba has a leg portion Z. Preferably, the front body Fr and the back body Ba each have a leg portion Z.

With reference to FIGS. 16 and 17, the intermediate region L has no flap in the central portion due to extension of the inner member 10. The leg portion according to the present invention accordingly does not extend over the entire bundled length but discontinues in the middle.

As shown in FIG. 15(a), the joint area rate indicating the rate of the total area of the joints 40 contained in the unit area in the outer member 20 composed of the stretchable sheet preferably differs between the leg portion Z and the region Q adjoined to the leg portion.

A small joint area rate leads to a large stretching stress, as described above. A combination of a leg portion Z with a small joint area rate causing a large stretching stress and a region Q adjoined to the leg portion with a large joint area rate causing a small stretching stress generates large stretching force acting on the leg portion Z, and thus produces a diaper having satisfactory fitness.

Alternatively, the joint area may vary within the leg portion Z.

With reference to FIG. 15(b), for example, the joint area rate indicating the rate of total area of joints contained in the unit area may differ between the section of the leg portion closer to the inner end point of the torso region T in the front-back direction and the section of the leg portion closer to the center side of the intermediate region L.

In this case, the section of the leg portion closer to the inner end point (the section Z1 in FIG. 15(b)) in the front-back direction of the torso region has a joint geometry that facilitates stretching in the width direction and the section of the leg portion closer to the center side of the intermediate region (the section Z2 in FIG. 15(b)) has a joint geometry that facilitates stretching in the diagonally upward direction.

With reference to FIG. 15(c), a section adjacent to the leg line 29 of the leg portion has a small joint area rate causing a large stretching stress, whereas a section remote from the leg line 29 of the leg portion Z has a large joint area rate causing a small stretching stress.

In this configuration, the closer the section is to the leg line of the leg portion, the larger stretching force applied to the section, which results in satisfactory fitness.

A pitch length r of the joints along the leg line 29 greater than the pitch length q of the joints in the width direction D the leg portion Z can achieve smooth stretching along the leg line 29.

As shown in FIG. 16, the following relation holds: torso region T=waist portion 23 underpart portion TX. In the depicted embodiment, the waist portion 23 has the turn-up portion 20C.

Turn-up of the geometry of the joints 40 in the underpart portion TX may generate a too large stretching stress in some cases. As shown in FIG. 16, this problem can be solved by a joint area rate of the waist portion 23 which is lower than the joint area rate of the underpart portion TX for achieving a lower stretching stress.

The waist portion 23 thereby has an appropriate stretching stress that is not too large but larger than the stretching stress of the underpart portion TX.

<Front and Rear Cover Sheets>

With reference to FIG. 18, front and back cover sheets 50, 60 may be provided to cover the front and back end portions of the inner member 10 attached to the internal face of the outer member 20 to prevent leakage from the front and rear edges of the inner member 10. In more detail, the front cover sheet 50 extends over the entire width of the front body F on the internal face of the front body F from the internal face of the turn-up section 20C at the waist-side end of the front body F to a position overlapping with the front end portion of the inner member 10. The back cover sheet 60 extends on the internal face of the back body Ba over the entire width, and extends over the entire width of the back body B from the internal face of the turn-up section 20C at the waist-side end of the back body B to a position overlapping with the back end portion of the inner member 10, in the embodiment illustrated in the drawings. Minor non-bonded regions are provided over the entire width (or only at the central portion) at side edge portions of the front and back cover sheets 50 and 60 at the crotch portion-side. The front and back cover sheets 50 and 60 having such non-bonded regions can prevent leakage of the adhesive and function as barriers against leakage when slightly suspended from the front face sheet.

As shown in the embodiment illustrated in the drawings, the front and rear cover sheets 50, 60 as separate components advantageously enlarge the range of choice of material, but disadvantageously needs additional materials and manufacturing processes. Thus, the turn-up portion 20C formed by turning up the outer member 20 toward the inner surface side of the diaper are respectively extended to portions overlapping with the inner member 10, so as to have the same function as that of the cover sheets 50, 60.

<Adhesion Test>

The first sheet layer and second sheet layer used were spunbond nonwoven fabric having a basis weight of 17 g/m$^2$ made of PE/PP conjugate fiber (core: polypropylene (melting point, 165° C.), sheath: polyethylene (melting point, 130° C.)), The elastic film used had a basis weight of 35 g/m$^2$, thickness of 35 μm, and a melting point in the range of 110 to 120° C. The elastic film in a natural-length state (the natural state or stretched state does not affect the relative comparison of the peel strength) was disposed between the first and second sheet layers in the same machine direction (MD). With reference to FIG. 29(a), rectangular joints 40 having long sides in the MD (short side: 1.0 mm, long side: 1.5 mm) are formed at an interval of 1 mm in the cross direction (CD) perpendicular to the MD and an interval of 17 mm in the MD with a stapler-type ultrasonic sealing machine (HARURU SUH-30 available from SUZUKI). A sample 100 provided with the elastic film having a CD length 100y of 80 mm and a MD length 100x of 50 mm was thereby produced (inventive example). The same operator carried out ultrasonic sealing for a pressuring time of about three seconds under the same pressure. The MD of the nonwoven fabric represents the direction of the orientation of the nonwoven fabric (the fibers of the nonwoven fabric are oriented in the MD), and can be determined, for example, by a method of testing the orientation of fiber by a zero-distance tensile strength in accordance with a TAPPI standard T481 or a simplified testing methods that determines the direction of the orientation from the ratio of the tensile strengths of the front-back direction to the width direction.

A sample was prepared in the same way as in the inventive example except a double layered structure free from the elastic film was used (comparative example). The structure of the sample free from the elastic film is regarded as the structure shown in Patent Literature 1 in which the first sheet layer is bonded to second sheet layer without an elastic film, in terms of peel strength.

With reference to FIG. 29(b), the first and second sheet layers were each manually peeled by a length 101z, 30 mm, from one end in the CD, each of the samples 100 has the laminated stretchable structures, the released portions 101 were clamped with chucks for a tensile testing machine, and peeling of the remaining 50 mm of the first and second sheet layers was re-started from the above mentioned 30 mm position at a chuck interval of 50 mm and a speed of testing of 300 mm/min in the stretchable direction. The observed maximum tensile stress was defined as peel strength. The testing machine was a universal TENSILON tester RTC-1210A available from ORIENTEC.

The results demonstrate that the inventive sample has a significantly high peel strength of 10.2N, whereas the comparative sample has a peel strength of 2.7N.

This stretchable structure 20X can also be applied to tape-type disposable diapers in addition to underpants-type disposable diapers.

Figure 29:
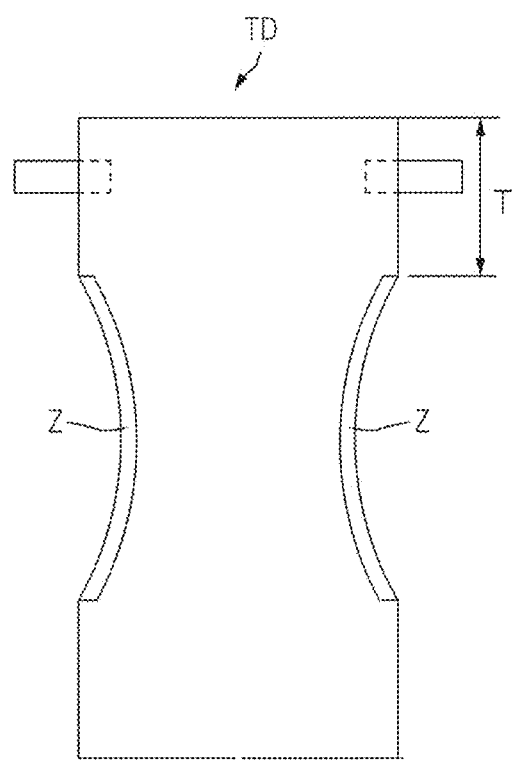
FIG. 29 is an outline plan view illustrating a tape-type disposable diaper in an unfolded state.

With reference to FIG. 29, for example, a tape-type disposable diaper TD1 having tapes on the two dorsal sides may have stretchable structures along leg portions Z.

The tape-type disposable diaper may have any overall structure known to persons skilled in the art, and redundant illustration of the drawing and redundant description are not repeated. The absorber and the top sheet may be composed of any material and have any structure as appropriately.

An example of the tape-type disposable diaper is of a so-called "loincloth or G-string" type that includes a lone tape for wrapping the front body of a wearer. The tape-type disposable diaper may be of a so-called "straight type" having two straight side edges.

Terminology in Specification

The terms used in the specification have the following meanings unless otherwise stated.

"Stretch rate" represents a value relative to the natural-length (100%).

"Basis weight" is determined as follows: After the sample or test piece is preliminarily dried, it is allowed to stand in a testing chamber or machine under the standard condition (temperature: 20±5° C., relative humidity: 65% or less) until the constant mass. The preliminary drying represents that the sample or test piece reaches constant mass in an environment within a relative humidity of 10 to 25% and at a temperature not exceeding 50° C. The fiber of an official regain of 0.0% does not need preliminary drying. A cut sample with a size of 200 mm by 250 mm (±2 mm) is prepared from the test piece after the constant mass with a cutting template (200 mm by 250 mm, ±2 mm). The sample is weighed and the weight is multiplied by 20 into the weight per square meter. The resulting value is defined as basis weight.

"Thickness" is automatically determined with an automatic thickness gauge (KES-G5 handy compression measurement program) under the conditions of a load of 10 gf/cm$^2$ and a pressurization area of 2 cm$^2$.

The test and measurement are carried out in a testing chamber or machine under the standard condition (temperature: 20±5° C., relative humidity: 65% or less) unless otherwise stated.

INDUSTRIAL APPLICABILITY

The present invention is applicable to underpants-type disposable diapers as described above, and is further applicable to a variety of absorbent articles having stretchable structures, such as tape-type and pad-type disposable diapers and sanitary napkins. The stretchable sheet of the present invention is also applicable to assistant materials, such as tapes for tape-type disposable diapers.

REFERENCE NUMERALS

A to E: Domain, Ba: back body, Fr: front body, L: intermediate region, Z: leg portion, 10: inner member, 11: liquid-pervious front face sheet, 12: liquid-impervious back face sheet, 13: absorber, 14: package sheet, 15: gather nonwoven fabric, 16: gather elastic member, 20: outer member, 21: first sheet layer, 22: second sheet layer, 20C: turn-up portion, 20X: stretchable structure, 24: waist elastic member, 25: contracted wrinkle, 29: leg line, 30: elastic film, 31: through hole, 40: joint, 70: non-stretchable region, 80: stretchable region, 81: main stretchable section, 82: buffer stretchable section.

The invention claimed is:
1. A disposable diaper having a stretchable region ventrodorsally, the region being stretchable in a width direction, comprising:
 a front torso region, a rear torso region, and an intermediate region disposed between the front torso region and the rear torso region, wherein
 leg portions are formed by narrowing the intermediate portion toward a center side in the width direction from inner end points of the torso region in a front-back direction over the intermediate portion,
 the leg portions reside at parts of a stretchable sheet stretchable in the width direction,
 the stretchable sheet comprises a laminate of a non-stretchable first sheet layer, a non-stretchable second sheet layer, and an elastic film disposed between the first sheet layer and the second sheet layer, the elastic film being stretchable in the width direction, the first sheet layer being bonded to the second sheet layer at a large number of joints directly or through the elastic film, the joints being arrayed at intervals,
 the stretchable sheet is contracted by a contraction force of the elastic film and can be stretched by an external force applied in the width direction, and
 the leg portions are also contracted by the contraction force of the elastic film and can be stretched by the external force applied in the width direction.
 wherein the leg portions and regions adjoined to the leg portions have different joint area rates that indicate rates of total areas of the joints contained in a unit area and thereby have different stretching stresses.

2. The disposable diaper according to claim 1, wherein the joints have a staggered arrangement.

3. A disposable diaper having a stretchable region ventrodorsally, the region being stretchable in a width direction, comprising:
 a front torso region, a rear torso region, and an intermediate region disposed between the front torso region and the rear torso region, wherein
 leg portions are formed by narrowing the intermediate portion toward a center side in the width direction from inner end points of the torso region in a front-back direction over the intermediate portion,
 the leg portions reside at parts of a stretchable sheet stretchable in the width direction,
 the stretchable sheet comprises a laminate of a non-stretchable first sheet layer, a non-stretchable second sheet layer, and an elastic film disposed between the first sheet layer and the second sheet layer, the elastic film being stretchable in the width direction, the first sheet layer being bonded to the second sheet layer at a large number of joints directly or through the elastic film, the joins being arrayed at intervals,
 the stretchable sheet is contracted by a contraction force of the elastic film and can be stretched by an external force applied in the width direction, and
 the leg portions are also contracted by the contraction force of the elastic film and can be stretched by the external force applied in the width direction,
 wherein a section of the leg portion closer to the inner end point of the torso region in the front-back direction and a section of the leg portion closer to the center side of the intermediate region have different joint area rates that indicate rates of total areas of the joints contained in a unit area.

4. A disposable diaper having a stretchable region ventrodorsally, the region being stretchable in a width direction, comprising:
 a front torso region, a rear torso region, and an intermediate region disposed between the front torso region and the rear torso region, wherein
 leg portions are formed by narrowing the intermediate portion toward a center side in the width direction from inner end points of the torso region in a front-back direction over the intermediate portion,
 the leg portions reside at parts of a stretchable sheet stretchable in the width direction,
 the stretchable sheet comprises a laminate of a non-stretchable first sheet layer, a non-stretchable second sheet layer, and an elastic film disposed between the first sheet layer and the second sheet layer, the elastic film being stretchable in the width direction, the first sheet layer being bonded to the second sheet layer at a large number of joints directly or through the elastic film, the joints being arrayed at intervals,
 the stretchable sheet is contracted by a contraction force of the elastic film and can be stretched by an external force applied in the width direction, and the leg portions are also contracted by the contraction force of the elastic film and can be stretched by the external force applied in the width direction, wherein a section adjacent to a leg line of the leg portion has a small joint area rate causing a large stretching stress, and a section remote from the leg line of the leg portion has a large joint area rate causing a small stretching stress.

* * * * *